US012760059B2

(12) United States Patent
Micalizio

(10) Patent No.: US 12,760,059 B2
(45) Date of Patent: Oct. 13, 2026

(54) GLUCOCORTICOID RECEPTOR MODULATORS

(71) Applicant: TRUSTEES OF DARTMOUTH COLLEGE, Hanover, NH (US)

(72) Inventor: Glenn C. Micalizio, Norwich, VT (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 858 days.

(21) Appl. No.: 17/923,466

(22) PCT Filed: May 7, 2021

(86) PCT No.: PCT/US2021/031308
§ 371 (c)(1),
(2) Date: Nov. 4, 2022

(87) PCT Pub. No.: WO2021/226465
PCT Pub. Date: Nov. 11, 2021

(65) Prior Publication Data

US 2023/0212215 A1 Jul. 6, 2023

Related U.S. Application Data

(60) Provisional application No. 63/177,208, filed on Apr. 20, 2021, provisional application No. 63/022,060, filed on May 8, 2020.

(51) Int. Cl.

| | |
|---|---|
| ***C07J 43/00*** | (2006.01) |
| *A61P 25/04* | (2006.01) |
| *A61P 25/24* | (2006.01) |
| *A61P 25/28* | (2006.01) |
| *A61P 27/06* | (2006.01) |
| *A61P 35/00* | (2006.01) |

(52) U.S. Cl.
CPC .................................. *C07J 43/003* (2013.01)

(58) Field of Classification Search
CPC ..................................................... C07J 43/003
See application file for complete search history.

(56) References Cited

U.S. PATENT DOCUMENTS

| | | | |
|---|---|---|---|
| 7,414,043 | B2 | 8/2008 | Kosemund et al. |
| 11,459,353 | B2 | 10/2022 | Micalizio |
| 11,512,107 | B2 | 11/2022 | Micalizio |
| 11,787,835 | B2 | 10/2023 | Micalizio |
| 12,065,465 | B2 | 8/2024 | Micalizio |
| 2019/0218246 | A1 | 7/2019 | Sun et al. |

FOREIGN PATENT DOCUMENTS

| | | | |
|---|---|---|---|
| WO | 2017112904 | A1 | 6/2017 |
| WO | 2020051329 | A1 | 3/2020 |

*Primary Examiner* — Susanna Moore
(74) *Attorney, Agent, or Firm* — Neal, Gerber & Eisenberg LLP

(57) ABSTRACT

The present disclosure relates to polycyclic (e.g., tetracyclic) glucocorticoid receptor (GR) modulators, synthetic methods for preparing such GR modulators, and methods of using such GR modulators to treat a glucocorticoid-dependent condition, such as cancer or hypercortisolism. Exemplary compounds have quaternary centers at C9 and C13 in which the quaternary center at C9 projects a substituent on the opposite face of the tetracycle as the substituent at C13.

13 Claims, 1 Drawing Sheet

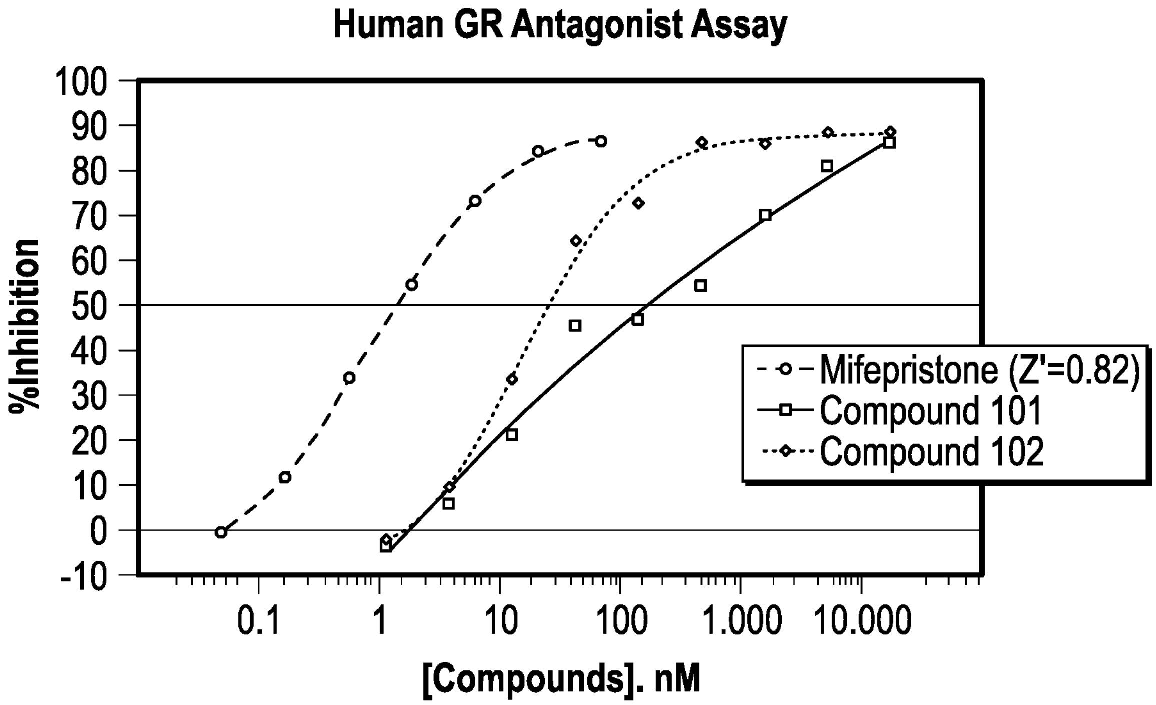
Human GR Antagonist Assay
100
90
80
70
60
50
40
30
20
10
0
-10
%Inhibition
0.1
1
10
100
1.000
10.000
[Compounds]. nM
Mifepristone (Z'=0.82)
Compound 101
Compound 102

GLUCOCORTICOID RECEPTOR MODULATORS

CROSS REFERENCE TO RELATED APPLICATIONS

This patent application is a National Stage Entry of International Application No. PCT/US2021/031308, filed on May 7, 2021, which claims priority to U.S. Provisional Patent Application No. 63/022,060, filed on May 8, 2020 and U.S. Provisional Patent Application No. 63/177,208, filed on Apr. 20, 2021, the entire contents of which are fully incorporated herein by reference.

FEDERALLY SPONSORED RESEARCH OR DEVELOPMENT

This invention was made with government support under R01 GM080266 awarded by the National Institutes of Health and R35 GM134725 awarded by the National Institutes of Health. The government has certain rights in the invention.

FIELD OF THE INVENTION

The present disclosure provides a new class of glucocorticoid receptor modulators and their use to treat glucocorticoid-dependent conditions, including malignancies that are dependent (at least in part) on the glucocorticoid receptor, including prostate cancer, pancreatic cancer, breast cancer, lung cancer, and ovarian cancer as well as hypercortisolism.

The present disclosure also provides concise synthetic methods for stereoselective assembly of polycyclic (e.g., tetracyclic) steroid and steroid-like (steroid numbering) compounds. The methods address stereoselection for C9-C10 bond formation and provide compounds having a quaternary center at C9. Certain compounds accessible by such synthetic methods are glucocorticoid receptor modulators.

BACKGROUND OF THE INVENTION

The glucocorticoid receptor (GR) is a member of the nuclear receptor superfamily of ligand-dependent transcription factors. Ligand-occupied GR induces or represses the transcription of thousands of genes by direct binding to DNA response elements and/or by physically associating with other transcription factors. GR mediates responses to glucocorticoid hormones involved in regulating a range of cellular functions, such as metabolism, cell growth and differentiation.

Several medical conditions are known to be dependent on, or sensitive to, the presence of GR activity.

GR is overexpressed across over 20 advanced solid tumors including prostate, pancreatic, triple negative breast (TNBC) and ovarian cancers. Emerging evidence suggests that glucocorticoids may contribute to failure of chemotherapy and tumor progression of many types of solid tumors including TNBC and castration resistant prostate cancer (CRPC).

Hypercortisolism, also called Cushing syndrome, is caused by exposure to high levels glucocorticoids, such as cortisol. Exogenous hypercortisolism may result from the use of oral corticosteroid medication. Endogenous hypercortisolism may result from overproduction of cortisol; for example tumors that produce adrenocorticotropic hormone (ACTH) cause the adrenal gland to make too much cortisol.

The hallmark symptoms of hypercortisolism are progressive truncal obesity and insulin resistance due to chronically elevated glucocorticoid levels. The insulin resistance seen in Cushing syndrome causes its major symptoms (obesity, glucose intolerance, hypertension, and dyslipidemia); a similar mechanism may be responsible for metabolic syndrome, which is a cluster of biochemical and physiological abnormalities associated with the development of cardiovascular disease and type 2 diabetes, although patients who have metabolic syndrome by definition do not have ACTH or cortisol producing tumors.

Clinical use of glucocorticoid receptor modulators has been limited by numerous and potentially serious side effects. There have been attempts to develop GR modulators that preferentially mediate inhibition rather than activation of transcription. Such selective GR modulators, termed selective glucocorticoid receptor modulators (SGRM), include dagrocorat, fosdagrocorat, mapracorat, and AZD9567.

However, there remains a need for compounds that modulate glucocorticoid receptor activity and, particularly, compounds that modulate the glucocorticoid receptor for use in the treatment of glucocorticoid-dependent conditions, including proliferative diseases, such as cancer, and hypercortisolism.

Many presently available synthetic and semisynthetic routes to steroids and tetracyclic terpenoids (more broadly) are often complex, inefficient, and/or wholly incapable of producing advantageous collections (i.e., libraries) of highly oxygenated/functionalized target compositions necessary for advancement through modern drug development. Indeed, efficient de novo synthesis of "steroidal" systems, or tetracyclic terpenoid-inspired compositions of matter, remains a challenging problem in chemistry.

Thus, efficient and step-economical (i.e., concise), flexible, convergent, and enantiospecific methods of synthesizing synthetic nat- and/or ent-steroids having varying stereochemistry and substitution, and/or functionality that facilitates subsequent molecular perturbation processes (i.e., manipulation of functionality in each ring of the characteristic tetracyclic nucleus) at research and/or production scale are still needed.

One recent advance in this area is the establishment of a synthetic route from epichlorohydrin to steroidal tetracycles bearing a quaternary center at C9. See, e.g., Kim et al., Nat. Comm. 10, 2448 (2019); WO2020051329. This synthetic route comprises a modern metallacycle-mediated annulative cross-coupling, a C9-C10 bond-forming process (e.g., through a double-asymmetric Friedel-Crafts cyclization or an intramolecular Heck reaction), and, optionally, an oxidative rearrangement reaction. This platform allows for construction of central motifs of tetracyclic terpenoid carbocyclic backbones in just a handful of steps from an inexpensive and readily available chiral starting material (epichlorohydrin). Nevertheless, there is a need for additional synthetic routes for stereoselectively establishing a C9 quaternary center.

SUMMARY OF THE INVENTION

The present disclosure relates to polycyclic (e.g., tetracyclic) compounds, including compounds that serve as glucocorticoid receptor modulators. In certain embodiments, the compounds have a C19 steroidal scaffold. In other embodiments, compounds having a C19 steroidal scaffold enable access to further compounds based on, or derived from, the C19 scaffold. In certain embodiments, the compounds comprise a tetracycle having stereochemistry at C9 and/or C13 that is opposite to that of natural steroid hormones such as cortisol. For example, in some such embodiments, the compounds comprise a tetracycle having a C9-β-aralkyl and/or C13-α-alkyl steroidal structure.

The present disclosure also relates to the use of such compounds as biologically active (e.g., therapeutic) components in, for example, pharmaceutical compositions and/or directly as human and/or animal therapeutics and medicines. In certain embodiments, the compounds are glucocorticoid receptor antagonists and/or may be used to treat or prevent glucocorticoid-dependent conditions, including proliferative diseases, such as cancer, and hypercortisolism.

In one aspect, this disclosure provides a method for treating a glucocorticoid-dependent condition by administering a compound disclosed herein or a pharmaceutically acceptable salt or prodrug thereof to a patient in need thereof. In some embodiments, the compound is Compound 101. In some embodiments, the compound is Compound 102. In some embodiments, the glucocorticoid-dependent condition is a proliferative disease, such as cancer. In some embodiments, the glucocorticoid-dependent condition is hypercortisolism. In some embodiments, the compound is administered orally.

The compounds, pharmaceutical compositions comprising the compounds, and methods for treating or preventing conditions, disorders, or diseases by administering the compounds are further described herein.

The present disclosure relates to a precise sequence of chemical transformations that result in generating a steroidal C9-C10 bond with high levels of stereoselection. Thus, in one aspect, this disclosure provides a method for stereoselective assembly of polycyclic (e.g., tetracyclic) compounds, including compounds that serve as glucocorticoid receptor modulators. In certain embodiments, the method comprises hydroxy group protection and protodesilylation. In some embodiments, the method further comprises Brønsted acid-mediated regio- and stereoselective Friedel-Crafts cyclization to forge the "steroidal" C9-C10 bond and establish a quaternary center at C9. Certain compounds generated by this method have quaternary centers at C9 and C13. In some such embodiments, the compounds have a stereochemistry at C13 that is opposite to that of natural steroid hormones such as cortisol. In some such embodiments, the compounds comprise a C13-α-substituted tetracycle. In other such embodiments, the compounds comprise a C13-β-substituted tetracycle.

These and other objects of the invention are described in the following paragraphs. These objects should not be deemed to narrow the scope of the invention.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art.

FIG. 1 is a line graph showing the results of a human GR antagonist assay for mifepristone and Compounds A, 101, and 102.

DESCRIPTION OF THE INVENTION

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

In certain aspects, the present disclosure relates to compounds (and methods of making such compounds, compositions comprising such compounds, and methods of using such compounds) comprising a generic tetracyclic steroidal (A, B, C, D) ring structure, as follows:

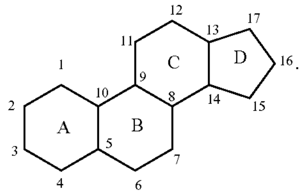

More particularly, the present disclosure relates to compounds (and methods of making such compounds, compositions comprising such compounds, and methods of using such compounds) comprising a generic C19 steroidal core skeleton of according to the following formulas, where additional substitution about these base structures is intended to be within the scope of the invention:

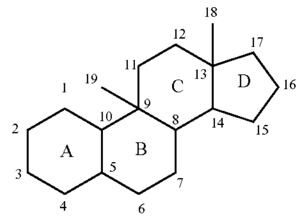

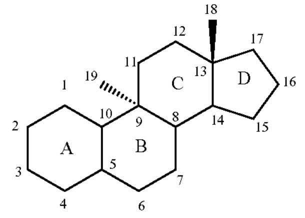

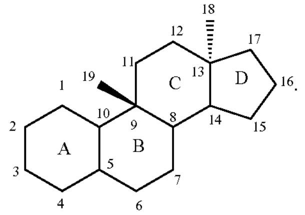

In one aspect, this disclosure provides compounds having a chemical structure including a C19 steroidal core skeleton, said C19 steroidal core skeleton having a quaternary center at each of carbon 09 and carbon 013. In some such embodiments, the "C18" group is attached at C13α, where the bond is shown as . In some such embodiments, the "C19" group is attached at C9β, where the bond is shown as .

By way of example, the C19 steroidal core skeleton depicted above encompasses, inter alia, a steroidal core skeleton, such as:

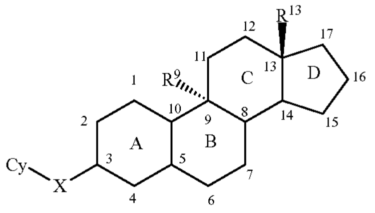

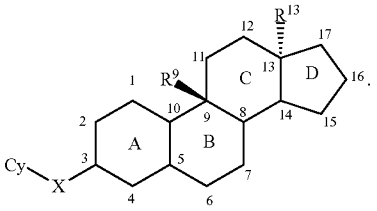

The numbering convention throughout the present disclosure is in accordance with numbered structures above.

In reference to the generic tetracyclic steroidal (A, B, C, D) ring structure and the generic C19 and C20 steroidal core skeletons, it will be well appreciated that in view of the disclosure contained herein as well as the teachings in the relevant fields of art, the compounds, compositions, and methods of the present disclosure are not limited to any particular respective constituent (R) group(s) at the various numbered carbon atoms. For example, an R group may be hydrogen, a $C_{1-10}$-aliphatic group, a $C_{6-10}$ aromatic group, carboxylic acid, carboxylic acid ester, hydroxyl, or halogen. Moreover, it will be well appreciated that in view of the disclosure contained herein as well as the teachings in the relevant fields of art, the compounds, compositions, and methods of the present disclosure may comprise ones in which any of the rings (A, B, C, D) can be saturated, partially unsaturated, or completely unsaturated (i.e., aromatic); in particular, the A ring can be saturated, partially unsaturated, or completely unsaturated; the B ring can be saturated or partially unsaturated; the C ring can be saturated or partially unsaturated; and the D ring can be saturated or partially unsaturated.

Thus, the C19 steroidal core skeleton depicted above also encompasses, inter alia, a steroidal core skeleton, such as:

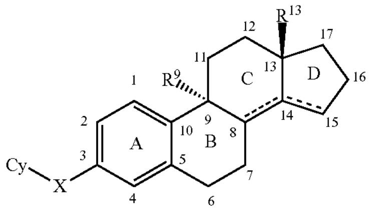

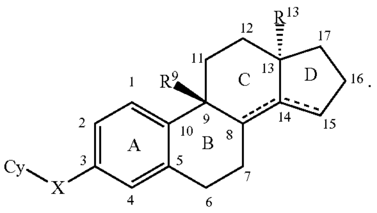

More particularly, the C19 steroidal core skeleton depicted above also encompasses, inter alia, a steroidal core skeleton, such as:

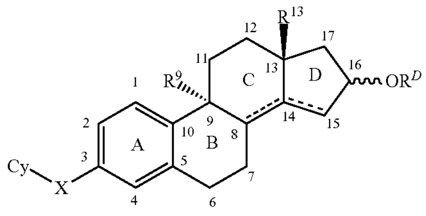

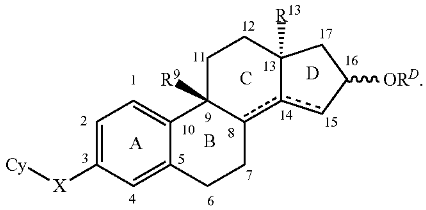

In certain embodiments, the —$OR^D$ substituent attached to carbon C16 by ∿∿∿ has the alpha orientation (e.g., ⋮⋮⋮). In certain other embodiments, the —$OR^D$ substituent attached to carbon C16 by ∿∿∿ has the best orientation (e.g., ◀).

In an exemplary embodiment, with reference to any of the above formulae, each of C1, C2, C4, C6, C7, C11, C12, C15, and C17 is independently substituted with hydrogen, $C_{1-10}$-alkyl, $C_{2-10}$-alkenyl, $C_{2-10}$-alkynyl, $C_{1-10}$-haloalkyl, halogen, oxo, hydroxy, $C_{1-6}$-alkoxy, —O—$C_{1-10}$-alkyl, —O—$C_{2-10}$-alkenyl, —O—$C_{2-10}$-alkynyl, —O—$C_{1-10}$-haloalkyl, —O—$C_{6-10}$-aryl, —O-5- to 10-membered heteroaryl, —OC(O)—$C_{1-10}$-alkyl, —OC(O)—$C_{6-10}$-aryl, —OC(O)-5- to 10-membered heteroaryl, $C_{6-10}$-aryl, or 5- to 10-membered heteroaryl and X, Cy, $R^9$, $R^{13}$, and $R^D$ are defined herein.

In one aspect, the present disclosure provides a method for preparing a C9-alpha-substituted or a C9-beta-substituted steroid-like compound (steroid numbering); in other words, generating a C9 quaternary center by way of C9-C10 bond formation. The method comprises initial desilylation at C11, and protection of free hydroxy groups (e.g., at C16), followed by a Brønsted acid-mediated regio- and stereoselective Friedel-Crafts cyclization reaction to form a C9-C10 bond and to set a quaternary center at C9.

The method described herein provides high levels of stereoselection in the C9-C10 bond forming process for a variety of substrates, including, but not limited to, optionally substituted alkyl groups attached at C9, wherein the alkyl group is optionally substituted with a non-hydrogen substituent such as $C_{6-10}$-aryl or —O—$(CH_2)_m$—$C_{6-10}$-aryl, where m is an integer selected from the group consisting of 0, 1, 2, and 3.

In one aspect, this disclosure provides a composition comprising a collection of synthetic stereoisomers defined by the C19 steroidal core skeleton depicted above, said C19 steroidal core skeleton having a quaternary center at each of carbon C9 and carbon C13, including stereoisomeric variation among the collection of synthetic stereoisomers; wherein the composition comprises greater than about 70%, alternatively greater than about 75%, alternatively greater than about 80%, alternatively greater than about 85%, alternatively greater than about 90%, or alternatively greater than about 95% of a single C9/C13 stereoisomer relative to other C9/C13 stereoisomers.

A. Definitions

As used in the specification and the appended claims, unless specified to the contrary, the following terms have the meaning indicated:

The term "about" as used herein, means approximately, and in most cases within 10% of the stated value.

The term "aliphatic" as used herein, includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups. In some embodiments, one or more units (e.g., methylene units) of an aliphatic may be replaced with —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, or —$NR^Z$C(S)—, where $R^Z$ is hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, $C_{3-8}$-cycloalkyl, and y is 0, 1, or 2. As will be appreciated by one of ordinary skill in the art, "aliphatic" is intended herein to include alkyl, alkenyl, alkynyl, cycloalkyl, and cycloalkenyl moieties.

The term "pharmaceutically acceptable" is used adjectivally to mean that the modified noun is appropriate for use as a pharmaceutical product for human use or as a part of a pharmaceutical product for human use.

The term "prodrug" refers to a compound that can be readily converted (e.g., metabolized) in vivo to yield a parent compound. Prodrugs include, but are not limited to, compounds having a substituent, such an ester moiety, which when metabolized yields a hydroxyl group. For example, compounds may have an ester moiety at C16 (steroid numbering), which yield a parent compound having a C16 hydroxyl upon in vivo conversion. For example, compounds may have an ester moiety at C17 (steroid numbering), which yield a parent compound having a C17 hydroxyl upon in vivo conversion. Exemplary ester moieties include, but are not limited to, an alkyl ester (e.g., —O—$C_{1-6}$-alkyl), a carbonate ester (e.g., —O—C(O)—O—$C_{1-10}$-alkyl), a carbamate ester (e.g.; —O—C(O)—$NR^{Z1}$ $R^{Z2}$), and a sulfamate ester (e.g., —$S(O)_2NR^{Z1}$ $R^{Z2}$). Additionally or alternatively, prodrugs may have a substituent, such as an optionally substituted 5- to 10-membered heteroaryl, attached to carbon C17 (steroid numbering), such as those identified in US2014/0371181 A1, which is herein incorporated by reference in its entirety. Prodrugs also include, but are not limited to, di-steroidal prodrugs such as those disclosed in U.S. Pat. No. 7,067,505, which is herein incorporated by reference in its entirety.

The terms "treat", "treating" and "treatment" refer to a method of alleviating or abrogating a condition, disorder, or disease and/or the attendant symptoms thereof.

B. Compounds

In one aspect, compounds disclosed herein possess biological activity, for example, as a modulator of the glucocorticoid receptor. In some such embodiments, compounds disclosed herein possess potent anti-glucocorticoid activity while substantially lacking agonistic activity. In another aspect, compounds disclosed herein provide a platform for development of analogs or derivatives possessing biological activity, for example, as modulators of the glucocorticoid receptor. Thus, in certain embodiments, a compound disclosed herein may be transformed by methods well known to those skilled in the art of synthetic organic chemistry into a derivative compound that possesses biological activity, for example, as a modulator of the glucocorticoid receptor.

In one aspect, compounds disclosed herein comprise a tetracyclic core. Attached to the tetracyclic core via an optional linker (X) is a cyclic (Cy), preferably a heterocyclic and more preferably a heteroaryl, moiety. In some such embodiments, Cy is attached via a single atom linker (e.g., —NR—, —O—, —S—) to tetracyclic C3. In other such embodiments, Cy is directly attached to tetracyclic C3, such as by C—C bond formation.

While the tetracyclic core appears to be "steroidal" in nature, it is fundamentally different than any known steroid. In certain embodiments, such compounds comprise a terminal cyclic, preferably aromatic, moiety (e.g., an aralkyl moiety) attached at C9 and positioned on the beta (p) face. In certain embodiments, such compounds comprise a moiety (e.g., an alkyl moiety) attached at C13 and positioned on the alpha (a) face. In certain embodiments, such compounds comprise a C8-C14 double bond in the C ring. In certain embodiments, such compounds comprise an alcohol or other group attached at C16 (rather than the typical C17 alcohol in natural steroid hormones such as cortisol). In particularly preferred embodiments, the compounds comprise an aralkyl moiety attached at C9β, a moiety attached at C13α, a C8-C14 double bond in the C ring, and an alcohol or ester moiety attached at C16. Such compounds unexpectedly act as glucocorticoid receptor antagonists. Exemplary generic formula include:

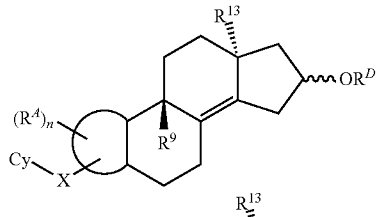

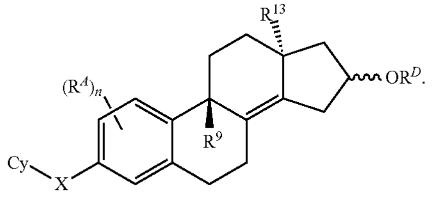

In one aspect, this disclosure provides a compound or a salt thereof, wherein the compound has a structure corresponding to Formula (I-A):

(I-A)

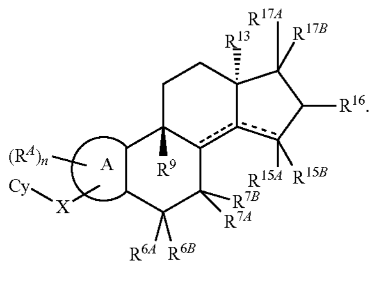

The compounds of Formula (I-A) optionally include a double bond between carbon C8 and carbon C14 (i.e., 8,14-unsaturated) or, alternatively, a double bond between carbon C14 and carbon C15, provided that if the bond between carbon C14 and carbon C15 is a double bond, then one of $R^{15A}$ or $R^{15B}$ is absent.

In certain embodiments, the compound has a structure corresponding to Formula (I-A1):

(I-A1)

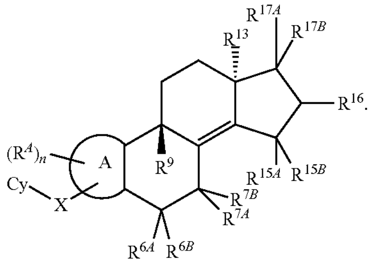

In one aspect, this disclosure provides a compound or a salt thereof, wherein the compound has a structure corresponding to Formula (II-A):

(II-A)

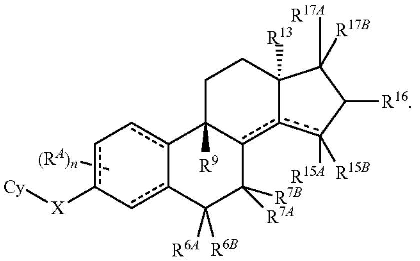

The compounds of Formula (II-A) have an unsaturated, partially saturated (e.g., cyclohexene or cyclohexadiene, such as where one double bond is between carbon C1 and carbon C2 and another double bond is between carbon C4 and C5), or saturated carbocyclic A ring containing six carbon atoms and optionally include a double bond between carbon C8 and carbon C14 (i.e., 8,14-unsaturated) or, alternatively, a double bond between carbon C14 and carbon C15, provided that if the bond between carbon C14 and carbon C15 is a double bond, then one of $R^{15A}$ or $R^{15B}$ is absent.

In certain embodiments, the compound has a structure corresponding to Formula (II-A1):

(II-A1)

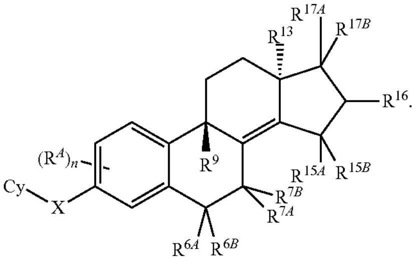

In one aspect, this disclosure provides a compound or a salt thereof, wherein the compound has a structure corresponding to Formula (III-A):

(III-A)

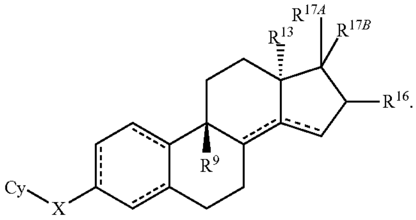

The compounds of Formula (III-A) have an unsaturated, partially saturated (e.g., cyclohexene or cyclohexadiene, such as where one double bond is between carbon C1 and carbon C2 and another double bond is between carbon C4 and C5), or saturated carbocyclic A ring containing six carbon atoms and optionally include a double bond between carbon C8 and carbon C14 (i.e., 8,14-unsaturated) or, alternatively, a double bond between carbon C14 and carbon C15.

In certain embodiments, the compound has a structure corresponding to Formula (III-A1):

(III-A1)

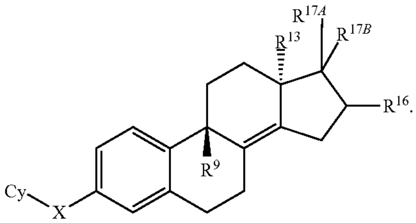

In one aspect, this disclosure provides a compound or a salt thereof, wherein the compound has a structure corresponding to Formula (IV-A):

(IV-A)

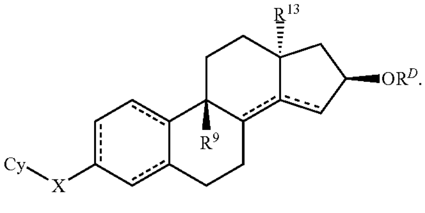

The compounds of Formula (IV-A) have an unsaturated, partially saturated (e.g., cyclohexene or cyclohexadiene, such as where one double bond is between carbon C1 and carbon C2 and another double bond is between carbon C4 and C5), or saturated carbocyclic A ring containing six carbon atoms and optionally include a double bond between carbon C8 and carbon C14 (i.e., 8,14-unsaturated) or, alternatively, a double bond between carbon C14 and carbon C15.

In certain embodiments, the compound has a structure corresponding to Formula (IV-A1):

(IV-A1)

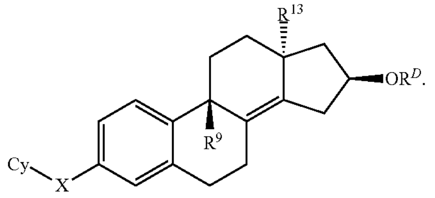

In any aspect or embodiment described herein, a solid semi-circle (e.g., representing the A ring) represents a saturated or unsaturated carbocyclic or heterocyclic ring containing 5 or 6 ring atoms. In some such embodiments, the A ring is optionally substituted benzene. In other such embodiments, the A ring is an optionally substituted 6-membered carbocyclic ring that is saturated or partially unsaturated. In some such embodiments, the A ring is optionally substituted cyclohexane. In some such embodiments, the A ring is optionally substituted cyclohexene. In some such embodiments, the A ring is optionally substituted cyclohexa-1,4-diene. In still other such embodiments, the A ring is a 5- or 6-membered heterocyclic ring, such as thiophene or furan.

In any aspect or embodiment described herein, variables shown in generic structures may have the following meanings:

Cy is an optionally substituted mono- or poly-cyclic moiety selected from the group consisting of $C_{6-15}$-aryl, 5- to 15-membered heteroaryl, $C_{3-15}$-cycloalkyl, $C_{3-15}$-cycloalkenyl, 3- to 15-membered heterocycloalkyl, and 3- to 15-membered heterocycloalkenyl;

X is absent or selected from the group consisting of —$NR^Z$—, —$C(R^Z)_2$—, —O—, —C(O)—, and —$S(O)_y$—, wherein each $R^Z$ is independently hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, or $C_{3-8}$-cycloalkyl, and y is 0, 1, or 2;

the A ring is an unsaturated, partially saturated, or saturated carbocyclic or heterocyclic ring containing 5 or 6 ring atoms;

m is an integer selected from the group consisting of 0, 1, 2, and 3;

n is an integer selected from the group consisting of 0, 1, 2, 3, 4, 5, and 6;

each $R^A$ is independently selected from the group consisting of hydrogen, $C_{1-10}$-alkyl, $C_{1-10}$-haloalkyl, $C_{2-10}$-alkenyl, $C_{2-10}$-alkynyl, halogen, oxo, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, wherein $R^{AX}$ is hydrogen, $C_{1-10}$-alkyl, $C_{1-10}$-haloalkyl, $C_{2-10}$-alkenyl, $C_{2-10}$-alkynyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}$ $R^{Z2}$, —$S(O)_2NR^{Z1}R^{Z2}$, —$S(O)_2R^{Z1}$, $C_{6-10}$-aryl, or 5- to 10-membered heteroaryl, wherein $R^{AY}$ is hydrogen, $C_{1-10}$-alkyl, $C_{1-10}$-haloalkyl, $C_{2-10}$-alkenyl, $C_{2-10}$-alkynyl, —C(O)—$C_{1-10}$-alkyl, —C(O)—$C_{6-10}$-aryl, —C(O)-heteroaryl, $C_{6-10}$-aryl, or 5- to 10-membered heteroaryl, wherein each of $R^Z1$ and $R^{Z2}$ are independently hydrogen, $C_{1-6}$-alkyl, $C_{1-10}$-haloalkyl, $C_{2-10}$-alkenyl, $C_{2-10}$-alkynyl, —$(CH_2)_m$—$C_{6-10}$-aryl, —$(CH_2)_m$-5- to 10-membered heteroaryl, hydroxy, or $C_{1-6}$-alkoxy;

each of $R^{6A}$ and $R^{6B}$ are independently absent or selected from the group consisting of hydrogen, $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, and halogen;

each of $R^{7A}$ and $R^{7B}$ are independently selected from the group consisting of hydrogen, $C_{1-10}$-alkyl, $C_{1-10}$-haloalkyl, $C_{2-10}$-alkenyl, $C_{2-10}$-alkynyl, halogen, hydroxy, and oxo;

$R^9$ is $C_{1-10}$-alkyl or $C_{1-10}$-haloalkyl, each of which is optionally interrupted by one or more of —O—, —$NR^Z$—, —C(O)—, —C(O)O—, —OC(O)—, —C(O)$NR^Z$—, and —$NR^Z$C(O)—; or $R^9$ is

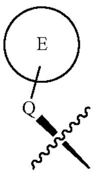

wherein Q is absent or selected from the group consisting of $C_1$-$C_{10}$-alkylene, $C_1$-$C_{10}$-haloalkylene, $C_2$-$C_{10}$-alkenylene, $C_2$-$C_{10}$-haloalkenylene, $C_2$-$C_{10}$-alkynylene, $C_2$-$C_{10}$-haloalkynylene, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$, —C(S)$NR^Z$—, —$NR^Z$C(S)—; and E is selected from the group consisting of $C_{6-10}$-aryl, 5- to 10-membered heteroaryl, $C_{3-8}$-cycloalkyl, or 3- to 8-heterocycloalkyl;

$R^{13}$ is selected from the group consisting of $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$, —$NR^ZS(O)_y$—, —C(S)$NR^Z$—, and —$NR^Z$C(S)—;

each of $R^{15A}$ and $R^{15B}$ are independently absent or selected from the group consisting of hydrogen, $C_{1-10}$-alkyl, $C_{2-10}$-alkenyl, $C_{2-10}$-alkynyl, $C_{1-10}$-haloalkyl, and halogen;

$R^{16}$ is selected from the group consisting of oxo and $X^{16}$—$R^D$, wherein $X^{16}$ is absent or selected from the group consisting of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, —$NR^Z$C(S)—, and $R^D$ is selected from the group consisting of hydrogen, $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, —$(CH_2)_m$—$C_{6-10}$-aryl, —$(CH_2)_m$-5- to 10-membered heteroaryl;

each of $R^{17A}$ and $R^{17B}$ are independently selected from the group consisting of hydrogen, $C_{1-10}$-alkyl, $C_{1-10}$-haloalkyl, $C_{2-10}$-alkenyl, $C_{2-10}$-alkynyl, halogen, hydroxy, $C_{1-6}$-alkoxy, $C_{1-10}$-alkyl-C(O), —C(O)—$C_{1-10}$-alkyl, —C(O)—$C_{1-10}$-hydroxyalkyl, —C(O)—$C_{1-10}$-alkyl-$C_{6-10}$-aryl, —C(O)—$C_{1-10}$-alkyl-heteroaryl, —C(O)—$C_{6-10}$-aryl, —C(O)-heteroaryl, —O—C(O)—$C_{1-6}$-alkyl, $C_{6-10}$-aryl, and 5- to 10-membered heteroaryl, or $R^{17A}$ and $R^{17B}$ together form an oxo; and each ---- independently represents a single bond or a double bond, provided that the bonds between C8-C14 and C14-C15 are not both double bonds;

wherein any $C_{6-10}$-aryl, 5- to 10-membered heteroaryl, $C_{3-8}$-cycloalkyl, or 3- to 8-heterocycloalkyl is optionally substituted with one or more halogen, hydroxy, $C_{1-6}$-alkyl, $C_{1-6}$-haloalkyl, or $C_{1-6}$-alkoxy.

In certain preferred embodiments, Cy is an optionally substituted aromatic monocyclic moiety selected from the group consisting of $C_{6-10}$-aryl and 5- to 10-membered heteroaryl. In some such preferred embodiments, Cy is a 5- to 10-membered heteroaryl optionally substituted with one or more halogen, hydroxy, $C_{1-6}$-alkyl, $C_{1-6}$-haloalkyl, or $C_{1-6}$-alkoxy. In some such preferred embodiments, Cy is a 6-membered heteroaryl, such as pyridinyl, pyridazinyl, pyrimidinyl, or pyrazinyl, optionally substituted with one or more $C_{1-6}$-alkyl. In some such preferred embodiments, Cy is pyridinyl, optionally substituted with one or two $C_{1-6}$-alkyl, such as methyl. In some such preferred embodiments, Cy is pyrimidinyl, optionally substituted with one or two $C_{1-6}$-alkyl, such as methyl. In some such preferred embodiments, Cy is pyrazinyl, optionally substituted with one or two $C_{1-6}$-alkyl, such as methyl.

In certain preferred embodiments, X is absent or selected from the group consisting of —$NR^Z$—, —O—, and —$S(O)_y$—, wherein $R^Z$ is hydrogen, $C_{1-6}$-alkyl, or $C_{1-6}$-haloalkyl, and y is 0, 1, or 2. In some such preferred embodiments, X is absent. In some such preferred embodiments, X is —$NR^Z$—, wherein $R^Z$ is hydrogen, $C_{1-6}$-alkyl, or $C_{1-6}$-haloalkyl. In some such preferred embodiments, X is —$NR^Z$—, wherein $R^Z$ is hydrogen, $C_{1-3}$-alkyl, or $C_{1-3}$-haloalkyl. In some such preferred embodiments, X is —NH—.

In certain preferred embodiments, the A ring is an unsaturated carbocyclic ring containing 6 ring atoms. In some such preferred embodiments, the A ring is phenyl.

In certain preferred embodiments, the A ring is a partially saturated or saturated carbocyclic ring containing 6 ring atoms. In some such preferred embodiments, the A ring is cyclohexadiene. In some such preferred embodiments, the A ring is cyclohexane.

In certain preferred embodiments, n is 0 or 1. In some such preferred embodiments, n is 0. In some such preferred embodiments, n is 1. In some such preferred embodiments, $R^A$ is $C_{1-10}$-alkyl or $C_{1-10}$-haloalkyl. In some such preferred embodiments, $R^A$ is $C_{1-6}$-alkyl or $C_{1-6}$-haloalkyl. In some such preferred embodiments, $R^A$ is $C_{1-3}$-alkyl or $C_{1-3}$-haloalkyl.

In certain preferred embodiments, m is 0 or 1. In some such preferred embodiments, m is 0. In some such preferred embodiments, m is 1.

In certain preferred embodiments, each of $R^{6A}$ and $R^{6B}$ are independently absent or selected from the group consisting of hydrogen, $C_{1-10}$-alkyl, $C_{1-10}$-haloalkyl, and halogen. In some such preferred embodiments, both $R^{6A}$ and $R^{6B}$ are hydrogen, one of $R^{6A}$ and $R^{6B}$ is hydrogen and the other of $R^{6A}$ and $R^{6B}$ is $C_{1-10}$-alkyl, one of $R^{6A}$ and $R^{6B}$ is hydrogen and the other of $R^{6A}$ and $R^{6B}$ is $C_{1-10}$-haloalkyl, or one of $R^{6A}$ and $R^{6B}$ is hydrogen and the other of $R^{6A}$ and $R^{6B}$ is halogen. In some such preferred embodiments, both $R^{6A}$ and $R^{6B}$ are hydrogen. In some such preferred embodiments, $R^{6A}$ is hydrogen and $R^{6B}$ is $C_{1-6}$-alkyl, such as methyl or ethyl. In some such preferred embodiments, $R^{6A}$ is hydrogen and $R^{6B}$ is halo, such as chloro or fluoro In certain preferred embodiments, each of $R^{7A}$ and $R^{7B}$ are independently absent or selected from the group consisting of hydrogen, $C_{1-10}$-alkyl, $C_{1-10}$-haloalkyl, and halogen. In some such preferred embodiments, both $R^{7A}$ and $R^{7B}$ are hydrogen, one of $R^{7A}$ and $R^{7B}$ is hydrogen and the other of $R^{7A}$ and $R^{7B}$ is $C_{1-10}$-alkyl, one of $R^{7A}$ and $R^{7B}$ is hydrogen and the other of $R^{7A}$ and $R^{7B}$ is $C_{1-10}$-haloalkyl, or one of $R^{7A}$ and $R^{7B}$ is hydrogen and the other of $R^{7A}$ and $R^{7B}$ is halogen. In some such preferred embodiments, both $R^{7A}$ and $R^{7B}$ are hydrogen. In some such preferred embodiments, $R^{7A}$ is hydrogen and $R^{7B}$ is $C_{1-6}$-alkyl, such as methyl or ethyl. In some such preferred embodiments, $R^{7A}$ is hydrogen and $R^{7B}$ is halo, such as chloro or fluoro.

In certain preferred embodiments, $R^9$ is $C_1$-$C_{10}$-alkyl or $C_1$-$C_{10}$-haloalkyl, each of which is optionally interrupted by one or more of —O—, —$NR^Z$—, —C(O)—, —C(O)O—, —OC(O)—, —C(O)$NR^Z$- and —$NR^Z$C(O)—. In some such embodiments, $R^9$ is $C_1$-$C_6$-alkyl or $C_1$-$C_6$-haloalkyl, each of which is optionally interrupted by one or more of —O—, —$NR^Z$—, —C(O)—, —C(O)O—, —OC(O)—, —C(O)$NR^Z$—, and —$NR^Z$C(O)—. In some such embodiments, $R^9$ is $C_1$-$C_3$-alkyl or $C_1$-$C_3$-haloalkyl, each of which is optionally interrupted by one or more of —O—, —$NR^Z$—, —C(O)—, —C(O)O—, —OC(O)—, —C(O)$NR^Z$—, and —$NR^Z$C(O)—. In some such embodiments, $R^9$ is $C_{1-6}$-alkyl or $C_{1-6}$-haloalkyl. In some such preferred embodiments, $R^9$ is $C_{1-6}$-alkyl. In some such embodiments, $R^9$ is $C_{1-3}$-alkyl or $C_{1-3}$-haloalkyl. In some such preferred embodiments, $R^9$ is $C_{1-3}$-alkyl. For example, $R^9$ may be methyl.

In certain preferred embodiments, $R^9$ is

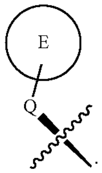

In certain preferred embodiments, Q is $C_1$-$C_{10}$-alkylene or $C_1$-$C_{10}$-haloalkylene, each of which is optionally interrupted by —O—, —C(O)—, —C(O)O—, or —OC(O)—. In some such embodiments, Q is $C_1$-$C_{10}$-alkylene or $C_1$-$C_{10}$-haloalkylene. In certain preferred embodiments, Q is $C_1$-$C_6$-alkylene or $C_1$-$C_6$-haloalkylene, each of which is optionally interrupted by —O—, —C(O)—, —C(O)O—, or —OC(O)—. In some such embodiments, Q is $C_1$-$C_6$-alkylene or $C_1$-$C_6$-haloalkylene.

In certain preferred embodiments, Q is $C_1$-$C_3$-alkylene or $C_1$-$C_3$-haloalkylene, each of which is optionally interrupted by —O—, —C(O)—, —C(O)O—, or —OC(O)—. In some such embodiments, Q is $C_1$-$C_3$-alkylene or $C_1$-$C_3$-haloalkylene. In some such preferred embodiments, Q is methylene. In some such embodiments, Q is $C_1$-$C_{10}$-alkylene interrupted by —O—. In some such embodiments, Q is $C_1$-$C_6$-alkylene interrupted by —O—. Thus, in some such preferred embodiments, Q is $C_1$-$C_6$-alkoxy.

In certain preferred embodiments, E is an optionally substituted $C_{6-10}$-aryl or 5- to 10-membered heteroaryl. In some such embodiments, E is an unsubstituted $C_{6-10}$-aryl, such as phenyl. In some such embodiments, E is a substituted $C_{6-10}$-aryl and the substituent(s) are selected from the group consisting of halogen, hydroxy, $C_{1-6}$-alkyl, $C_{1-6}$-haloalkyl, or $C_{1-6}$-alkoxy. In some such embodiments, E is a $C_{6-10}$-aryl substituted with $C_{1-6}$-alkoxy.

In certain preferred embodiments, $R^9$ is aralkyl. In some such preferred embodiments, Q-E is benzyl.

In certain preferred embodiments, $R^{13}$ is $C_1$-$C_{14}$-alkyl or $C_1$-$C_{14}$-haloalkyl, each of which is optionally interrupted by one or more of —O—, —$NR^Z$—, —C(O)—, —C(O)O—, —OC(O)—, —C(O)$NR^Z$- and —$NR^Z$C(O)—. In some such embodiments, $R^{13}$ is $C_{1-10}$-alkyl or $C_{1-10}$-haloalkyl. In some such preferred embodiments, $R^{13}$ is $C_{1-10}$-alkyl. In some such embodiments, $R^{13}$ is $C_{1-6}$-alkyl or $C_{1-6}$-haloalkyl. In some such preferred embodiments, $R^{13}$ is $C_{1-6}$-alkyl. In some such embodiments, $R^{13}$ is $C_{1-3}$-alkyl or $C_{1-3}$-haloalkyl.

In some such preferred embodiments, $R^{13}$ is $C_{1-3}$-alkyl. For example, $R^{13}$ may be methyl.

In certain preferred embodiments, the bond between C8-C14 is a double bond and the bond between C14-C15 is a single bond.

In certain preferred embodiments, the bond between C14-C15 is a single bond and each of $R^{15A}$ and $R^{15B}$ are independently selected from the group consisting of hydrogen, $C_{1-10}$-alkyl, $C_{1-10}$-haloalkyl, and halogen. In some such preferred embodiments, both $R^{15A}$ and $R^{15B}$ are hydrogen, one of $R^{15A}$ and $R^{15B}$ is hydrogen and the other of $R^{15A}$ and $R^{15B}$ is $C_{1-10}$-alkyl, one of $R^{15A}$ and $R^{15B}$ is hydrogen and the other of $R^{15A}$ and $R^{15B}$ is $C_{1-10}$-haloalkyl, or one of $R^{15A}$ and $R^{15B}$ is hydrogen and the other of $R^{15A}$ and $R^{15B}$ is halogen. In some such preferred embodiments, both $R^{15A}$ and $R^{15B}$ are hydrogen.

In certain preferred embodiments, $R^{16}$, if present is oxo or $OR^D$, and $R^D$ is hydrogen, $C_{1-10}$-alkyl, or $C_{1-10}$-haloalkyl. In some such preferred embodiments, $R^{16}$ is —OH, —O—$C_{1-6}$-alkyl, or —O—$C_{1-6}$-haloalkyl.

In certain preferred embodiments, each of $R^{17A}$ and $R^{17B}$ are independently selected from the group consisting of hydrogen, $C_{1-10}$-alkyl, $C_{1-10}$-haloalkyl, hydroxy, —C(O)—$C_{1-10}$-alkyl, —C(O)—$C_{1-10}$-hydroxyalkyl, and —O—C(O)—$C_{1-6}$-alkyl. In some such preferred embodiments, both $R^{17A}$ and $R^{17B}$ are hydrogen, one of $R^{17A}$ and $R^{17B}$ is hydrogen and the other of $R^{17A}$ and $R^{17B}$ is $C_{1-10}$-alkyl, one of $R^{17A}$ and $R^{17B}$ is hydrogen and the other of $R^{17A}$ and $R^{17B}$ is $C_{1-10}$-haloalkyl, one of $R^{17A}$ and $R^{17B}$ is hydrogen and the other of $R^{17A}$ and $R^{17B}$ is halogen, one of $R^{17A}$ and $R^{17B}$ is hydroxy and the other of $R^{17A}$ and $R^{17B}$ is —C(O)—$C_1$—O-hydroxyalkyl. In some such preferred embodiments, both $R^{17A}$ and $R^{17B}$ are hydrogen, one of $R^{17A}$ and $R^{17B}$ is —C(O)—$C_{1-10}$-alkyl, such as —C(O)-methyl, and the other of $R^{17A}$ and $R^{17B}$ is $C_{1-10}$-alkyl, such as methyl, or —O—C(O)—$C_{1-6}$-alkyl, such as —O—C(O)— methyl. In some such preferred embodiments, both $R^{17A}$ and $R^{17B}$ are hydrogen.

In certain preferred embodiments, Cy is an optionally substituted monocyclic 5- or 6-membered heteroaryl; X is absent or $NR^Z$—; Q is absent, $C_1$-$C_{10}$-alkylene, or $C_1$-$C_{10}$-haloalkylene, each of which is optionally interrupted by one or more of —O—, —$NR^Z$—, —C(O)—, —C(O)O—, —OC(O)—, —C(O)$NR^Z$—, and —$NR^Z$C(O)—; and E is an optionally substituted $C_{6-10}$-aryl. In some such embodiments, Q is absent. In some such embodiments, Q is $C_1$-$C_{10}$-alkylene, optionally interrupted by —O—, —C(O)—, —C(O)O—, or —OC(O)—. In some such embodiments, Q is $C_1$-$C_{10}$-alkylene, optionally interrupted by —O—. In some such embodiments, E is an unsubstituted $C_{6-10}$-aryl, such as phenyl. In some such embodiments, E is a substituted $C_{6-10}$-aryl and the substituent(s) are selected from the group consisting of halogen, hydroxy, $C_{1-6}$-alkyl, $C_{1-6}$-haloalkyl, or $C_{1-6}$-alkoxy. In some such embodiments, E is a $C_{6-10}$-aryl substituted with $C_{1-6}$-alkoxy.

It is to be understood that any preferred embodiment for a variable (e.g., Cy, X, m, n, $R^A$, $R^{6A}$, $R^{6B}$, $R^{7A}$, $R^{7B}$, $R^9$, Q, E, $R^{13}$, $R^{15A}$ $R^{15B}$ $R^{16}$, $R^{17A}$ and $R^{17B}$) may be combined with any preferred embodiment for any other variable(s) described herein. Exemplary combinations for compounds having a structure corresponding to formulae described herein include, but are not limited to: Cy is optionally substituted monocyclic 5- or 6-membered heteroaryl; X is absent or —$NR^Z$—; A ring is an unsaturated carbocyclic ring containing 6 ring atoms; n is 0 or 1; $R^A$, if present, is $C_{1-6}$-alkyl; $R^{6A}$ and $R^{6B}$ are both hydrogen; $R^{7A}$ and $R^{7B}$ are both hydrogen; $R^9$ is $C_{1-6}$-alkyl or aralkyl, preferably benzyl; $R^{13}$ is $C_{1-6}$-alkyl; the bond between C8-C14 is a double bond and the bond between C14-C15 is a single bond; $R^{15A}$ and $R^{15B}$ are both hydrogen; $R^{16}$ is —OH or —O—C(O)—$C_{1-6}$-alkyl; and $R^{17A}$ and $R^{17B}$ are both hydrogen. In particular, an exemplary combination for compounds having a structure corresponding to formulae described herein includes, but is not limited to: Cy is optionally substituted monocyclic 6-membered heteroaryl where the optional substituent is $C_{1-6}$-alkyl or $C_{1-6}$-haloalkyl; X is absent or —$NR^Z$—, where $R^Z$ is hydrogen, $C_{1-6}$-alkyl, or $C_{1-6}$-haloalkyl; A ring is an unsaturated carbocyclic ring containing 6 ring atoms; n is 0 or 1; $R^A$, if present, is $C_{1-6}$-alkyl; $R^{6A}$ and $R^{6B}$ are both hydrogen; $R^{7A}$ and $R^{7B}$ are both hydrogen; $R^9$ is $C_{1-6}$-alkyl or aralkyl, preferably benzyl; $R^{13}$ is $C_{1-6}$-alkyl; the bond between 08-014 is a double bond and the bond between C14-C15 is a single bond; $R^{15A}$ and $R^{15B}$ are both hydrogen; $R^{16}$ is —OH or —O—C(O)—$C_{1-6}$-alkyl; and $R^{17A}$ and $R^{17B}$ are both hydrogen In one aspect, this disclosure provides a compound or salt or prodrug thereof, wherein the compound has a structure corresponding to one of the compounds listed in Table A:

Data for select compounds are shown in Table A:

| Cmpd | Structure | $EC_{50}$ (nM) | cLogP |
|---|---|---|---|
| A | 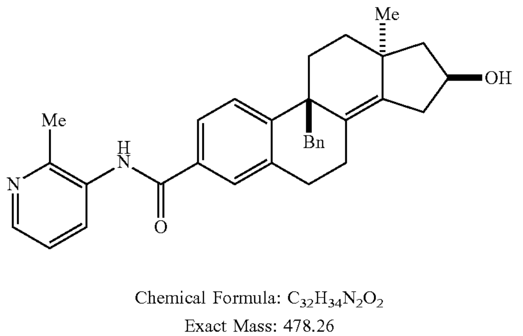 Chemical Formula: $C_{32}H_{34}N_2O_2$ Exact Mass: 478.26 Molecular Weight: 478.64 m/z: 478.26 (100.0%), 479.27 (35.1%), 480.27 (6.4%) Elemental Analysis: C, 80.30; H, 7.16; N, 5.85; O, 6.69 | not active | 5.4 |

-continued

| Cmpd | Structure | $EC_{50}$ (nM) | cLogP |
|---|---|---|---|
| 101 | 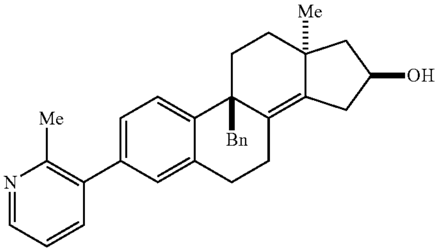 [SMILES: Cc1ncccc1-c1ccc2c(c1)CCC1=C3C[C@H](O)C[C@]3(C)CC[C@]12Cc1ccccc1]<br>Chemical Formula: $C_{31}H_{33}NO$<br>Exact Mass: 435.26<br>Molecular Weight: 435.61<br>m/z: 435.26 (100.0%), 436.26 (33.9%), 437.26 (5.8%)<br>Elemental Analysis: C, 85.48; H, 7.64; N, 3.22; O, 3.67 | <100 | 7 |
| 102 | 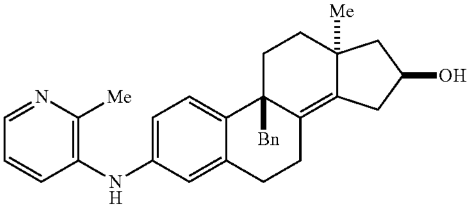 [SMILES: Cc1ncccc1Nc1ccc2c(c1)CCC1=C3C[C@H](O)C[C@]3(C)CC[C@]12Cc1ccccc1]<br>Chemical Formula: $C_{31}H_{34}N_2O$<br>Exact Mass: 450.27<br>Molecular Weight: 450.63<br>m/z: 450.27 (100.0%), 451.27 (34.0%), 452.27 (5.9%)<br>Elemental Analysis: C, 82.63; H, 7.61; N, 6.22; O, 3.55 | 16 | 7 |
| 103 | 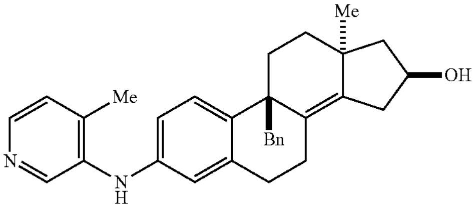 [SMILES: Cc1ccncc1Nc1ccc2c(c1)CCC1=C3C[C@H](O)C[C@]3(C)CC[C@]12Cc1ccccc1]<br>Chemical Formula: $C_{31}H_{34}N_2O$<br>Exact Mass: 450.27<br>Molecular Weight: 450.63<br>m/z: 450.27 (100.0%), 451.27 (34.0%), 452.27 (5.9%)<br>Elemental Analysis: C, 82.63; H, 7.61; N, 6.22; O, 3.55 | | 7 |
| 104 | 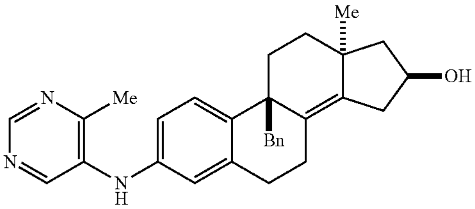 [SMILES: Cc1ncncc1Nc1ccc2c(c1)CCC1=C3C[C@H](O)C[C@]3(C)CC[C@]12Cc1ccccc1]<br>Chemical Formula: $C_{30}H_{33}N_3O$<br>Exact Mass: 451.26<br>Molecular Weight: 451.61<br>m/z: 451.26 (100.0%), 452.27 (32.9%), 453.27 (5.4%), 452.26 (1.1%)<br>Elemental Analysis: C, 79.79; H, 7.37; N, 9.30; O, 3.54 | | 5.5 |

-continued

| Cmpd | Structure | $EC_{50}$ (nM) | cLogP |
| --- | --- | --- | --- |
| 105 | 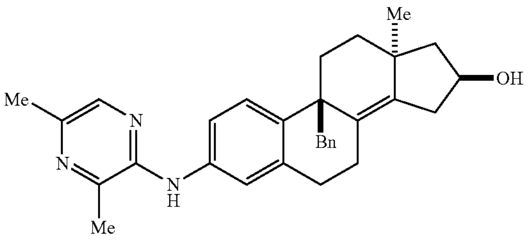 [SMILES: Cc1cnc(Nc2ccc3c(c2)CCC2=C4C[C@H](O)C[C@]4(C)CC[C@]23Cc2ccccc2)c(C)n1]<br>Chemical Formula: $C_{31}H_{35}N_3O$<br>Exact Mass: 465.28<br>Molecular Weight: 465.64<br>m/z: 465.28 (100.0%), 466.28 (35.1%), 467.28 (6.0%)<br>Elemental Analysis: C, 79.96; H, 7.58; N, 9.02; O, 3.44 | | 6 |
| 106 | 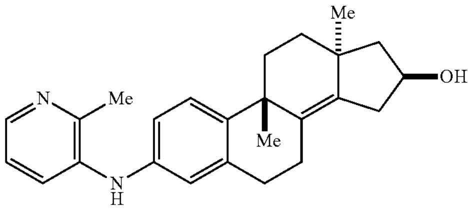<br>Chemical Formula: $C_{25}H_{30}N_2O$<br>Exact Mass: 374.24<br>Molecular Weight: 374.53<br>m/z: 374.24 (100.0%), 375.24 (27.4%), 376.24 (3.9%)<br>Elemental Analysis: C, 80.17; H, 8.07; N, 7.48; O, 4.27 | | 5.6 |

C. Synthetic Methods and Intermediates

The following general Scheme (A) is representative of a particular embodiment of the method and allows for concise and stereoselective synthesis of "C19" tetracyclic compounds:

Scheme (A)

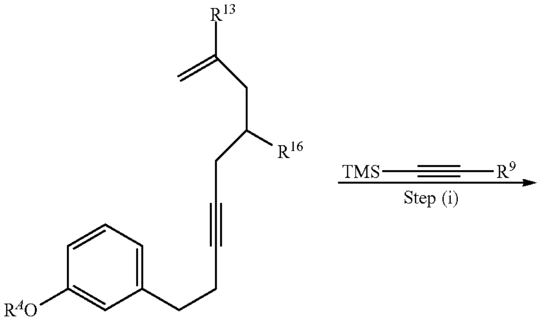

Enyne (a)

-continued

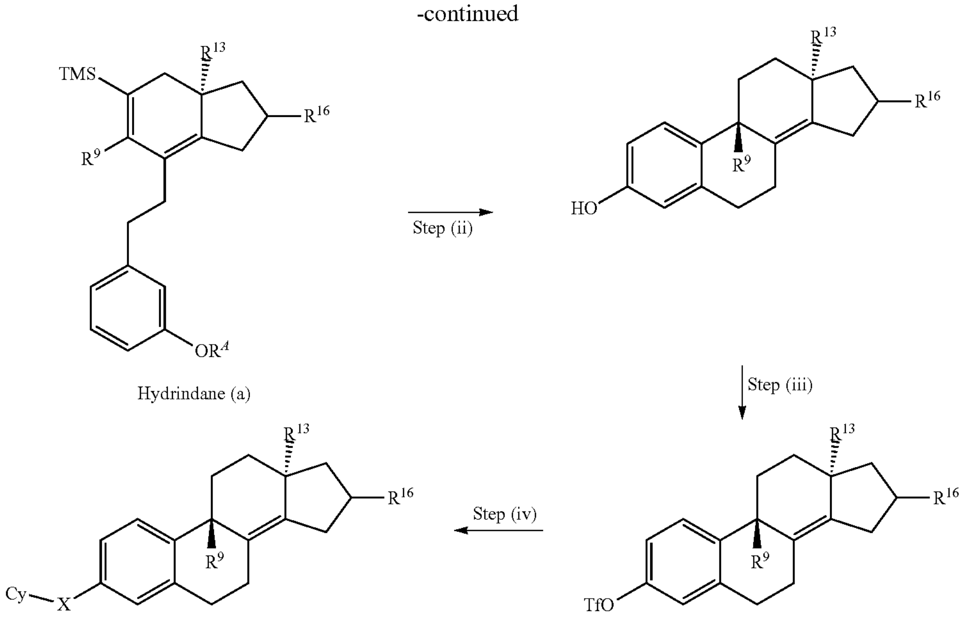

Step (i) is a metallacycle-mediated annulation reaction between readily available Enyne (a) and an optionally substituted alkyne (e.g., in the presence of Ti(Oi-Pr)$_4$, n-BuLi, and PhMe) to provide Hydrindane (a), which possesses the C13 quaternary center. While step (i) depicts an optionally substituted trimethylsilypropyne, alternative compounds such as those having a simple internal alkyne (without a TMS) or an alternative to the silyl group (or stannyl group, for example) on the alkyne may also be used.

Step (ii) is a cyclization reaction through C9-C10 bond-formation. Dealkylation (e.g., where $R^A$ is $C_{1-6}$-alkyl) can be performed using, for example, diisobutylaluminium hydride (DIBAL).

In one aspect, this disclosure provides a method for stereoselectively preparing a 9-alpha-substituted or a 9-beta-substituted steroid-like compound (steroid numbering). In certain embodiments, the method comprises the steps of (a) providing a protodesilylated, hydroxyl-protected substrate bearing an alkene at C9-C11 and a substituent at C9; and (b) performing a regio- and stereoselective cyclization reaction to form a C9-C10 bond and to set a quaternary center at C9.

The following general Schemes (1)-(6) are representative of particular embodiments of the method:

(1)

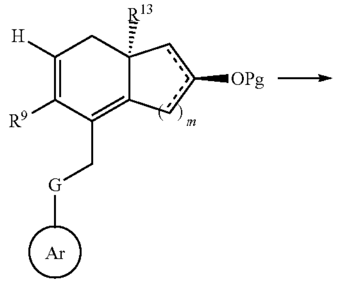

-continued

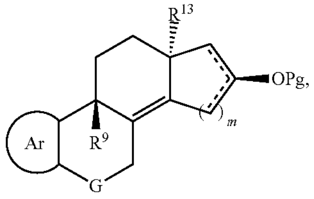

(2)

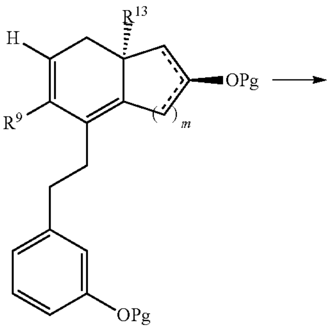

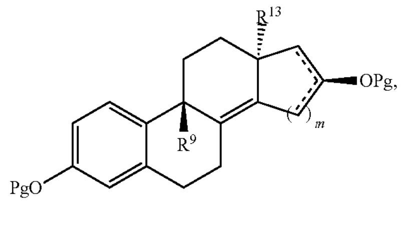

-continued (3)

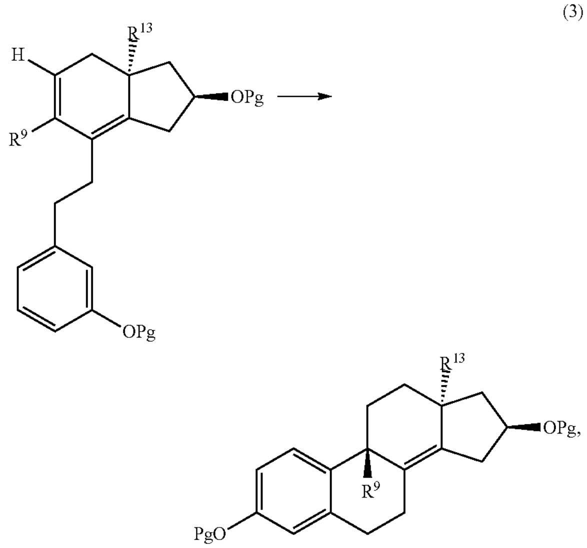

(4)

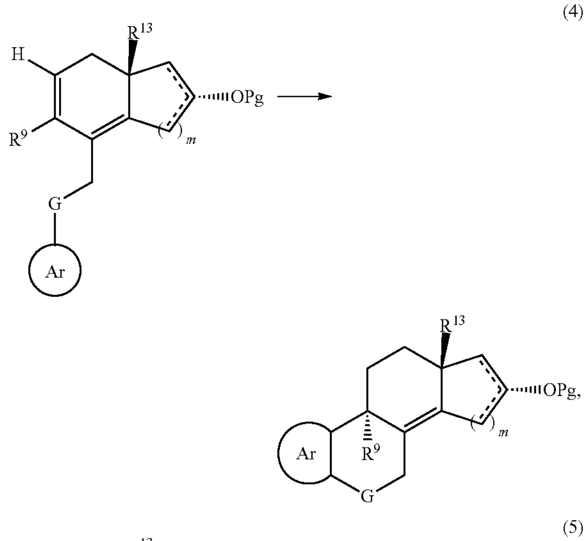

(5)

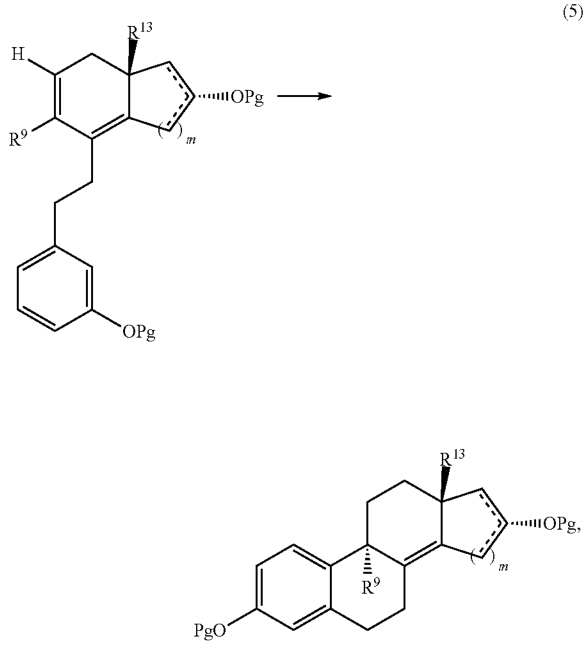

-continued (6)

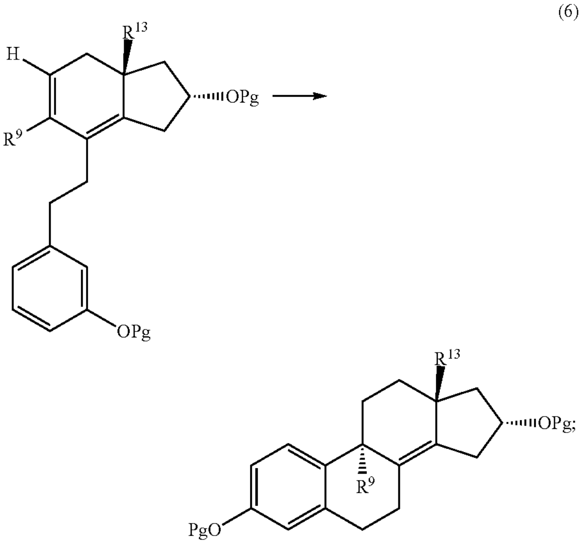

wherein m is an integer selected from the group consisting of 1, 2, and 3;

the Ar ring is a $C_{6-10}$-aryl or 5- to 10-membered heteroaryl and is optionally substituted with $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, oxo, or —OPg;

G is a substituted or unsubstituted carbon atom, a substituted or unsubstituted nitrogen atom, an oxygen atom, or a sulfur atom;

$R^9$ is selected from the group consisting of $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, and —$NR^Z$C(S)—, and

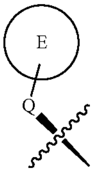

wherein Q is absent or selected from the group consisting of $C_1$-$C_{10}$-alkylene, $C_1$-$C_{10}$-haloalkylene, $C_2$-$C_{10}$-alkenylene, $C_2$-$C_{10}$-haloalkenylene, $C_2$-$C_{10}$-alkynylene, and $C_2$-$C_{10}$-haloalkynylene, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, —$NR^Z$C(S)—; and E is selected from the group consisting of $C_{6-10}$aryl, 5- to 10-membered heteroaryl, $C_{3-8}$-cycloalkyl, or 3- to 8-heterocycloalkyl;

$R^{13}$ is selected from the group consisting of $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, and $-NR^ZC(S)-$, $-(CH_2)_m-C_{6-10}$-aryl, and $-(CH_2)_m$-5- to 10-membered heteroaryl;

each Pg is an oxygen protecting group such as methyl, tert-butyloxycarbonyl (BOC), methoxymethyl (MOM), tert-butyldimethylsilyl (TBS), tert-butyldiphenylsilyl (TBDPS), or tribenzylsilyl;

wherein each $R^Z$ is independently hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, or $C_{3-8}$-cycloalkyl, and y is 0, 1, or 2.

Schemes (1)-(6) depict a regio- and stereoselective cyclization reaction to form a C9-C10 bond and to set a quaternary center at C9. In certain embodiments, the regio- and stereoselective cyclization reaction is a Freidel-Crafts cyclization reaction. In certain embodiments, the regio- and stereoselective cyclization reaction is a Brønsted acid-mediated reaction.

In certain embodiments, the methods depicted in Schemes (1)-(6) further comprise providing a protodesilylated, hydroxyl-protected substrate bearing an alkene at C9-C11 and a substituent at C9. In some such embodiments, the substrate is prepared by protodesilylation at C11 of a suitably functionalized precursor and protection of free hydroxyl groups.

In certain embodiments, the methods depicted in Schemes (1)-(6) further comprise one or more steps to remove oxygen protecting groups and/or introduce functionality at C3. In some such embodiments, the methods depicted in Schemes (1)-(6) further comprise a Suzuki coupling reaction to introduce a C—C bond at C3. In some such embodiments, the methods depicted in Schemes (1)-(6) further comprise a Pd-catalyzed C—N bond formation to introduce a C—N bond at C3.

In one aspect, this disclosure provides intermediate compounds useful in the synthesis of nuclear hormone receptor modulators and, particularly, GR modulators. In certain embodiments, the intermediate compounds comprise one or more oxygen protecting groups (e.g., at C16).

In certain embodiments, the intermediate compound has a structure corresponding to Formula (INT-1.1), Formula (INT-2.1), Formula (INT-3.1), Formula (INT-4.1), Formula (INT-5.1), or Formula (INT-6.1):

(INT-1.1)

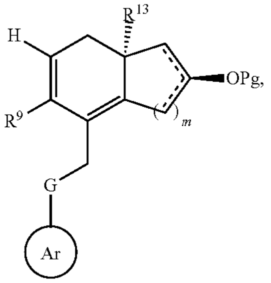

(INT-2.1)

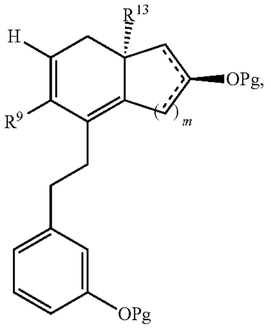

-continued (INT-3.1)

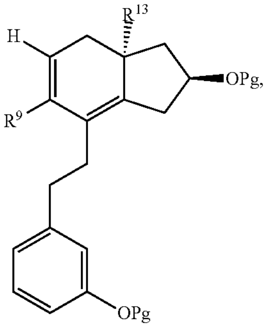

(INT-4.1)

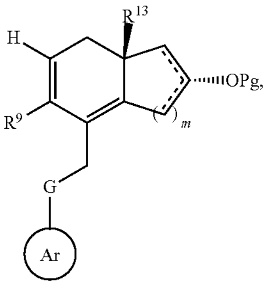

(INT-5.1)

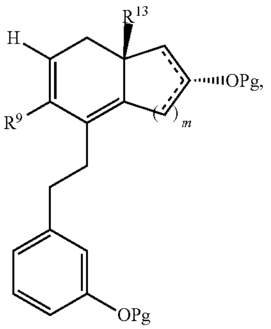

(INT-6.1)

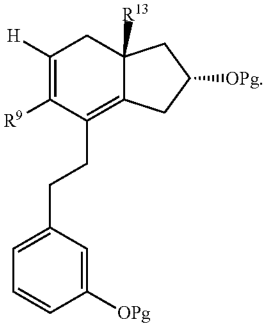

Some such intermediate compounds include compounds listed in Table B:
TABLE B
| Compound | Structure |
|---|---|
| 201 | 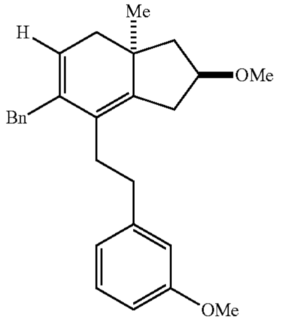 [SMILES: COc1cccc(CCC2=C3C[C@H](OC)C[C@]3(C)CC=C2Cc2ccccc2)c1] |
| 202 | 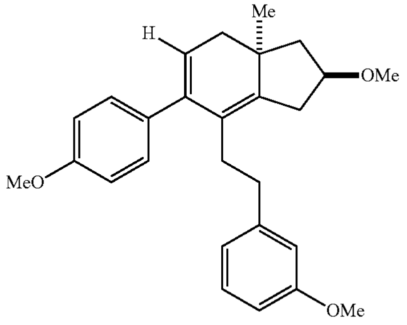 [SMILES: COc1ccc(C2=CC[C@@]3(C)C[C@@H](OC)CC3=C2CCc2cccc(OC)c2)cc1] |
| 203 | 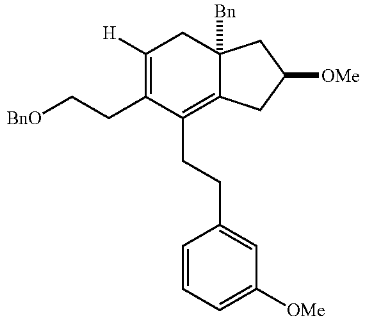 [SMILES: COc1cccc(CCC2=C3C[C@H](OC)C[C@]3(Cc3ccccc3)CC=C2CCOCc2ccccc2)c1] |
| 204 | 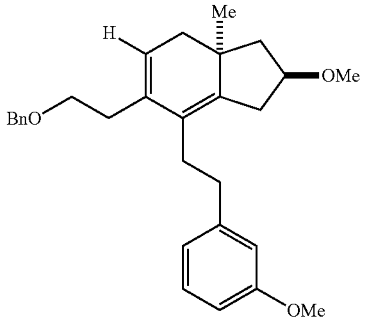 [SMILES: COc1cccc(CCC2=C3C[C@H](OC)C[C@]3(C)CC=C2CCOCc2ccccc2)c1] |
TABLE B-continued
| Compound | Structure |
|---|---|
| 205 | 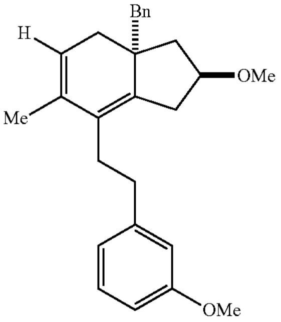 [SMILES: COc1cccc(CCC2=C3C[C@H](OC)C[C@]3(Cc3ccccc3)CC=C2C)c1] |
| 206 | 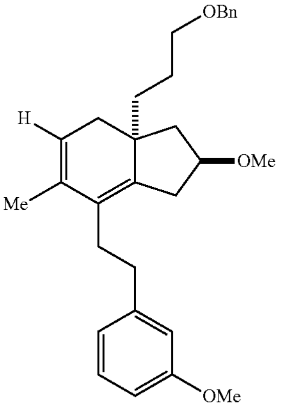 [SMILES: COc1cccc(CCC2=C3C[C@H](OC)C[C@]3(CCCOCc3ccccc3)CC=C2C)c1] |
| 207 | 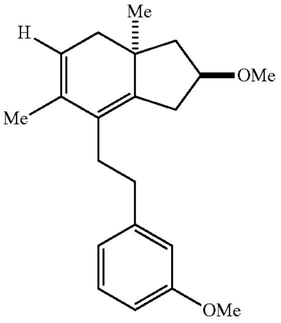 |
In certain embodiments, the intermediate compound has a structure corresponding to Formula (INT-1.2), Formula (INT-2.2), Formula (INT-3.2), Formula (INT-4.2), Formula (INT-5.2), or Formula (INT-6.2):
(INT-1.2)
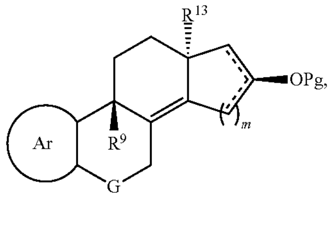

-continued
(INT-2.2)
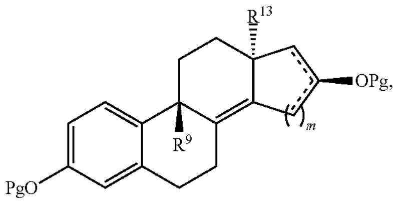
(INT-3.2)
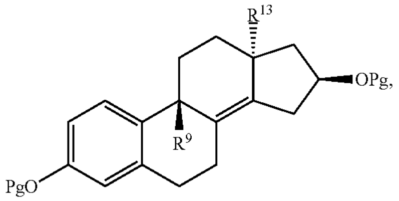
(INT-4.2)
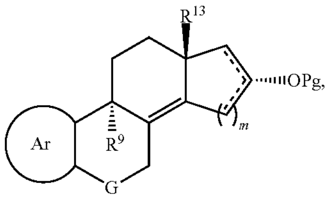
(INT-5.2)
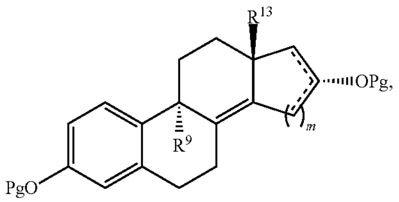
(INT-6.2)
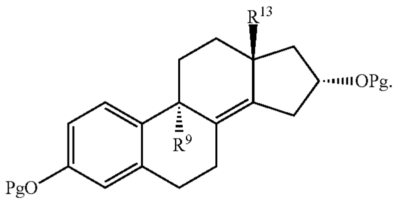
Some such intermediate compounds include compounds listed in Table C:
TABLE C
| Compound | Structure |
|---|---|
| 301 | 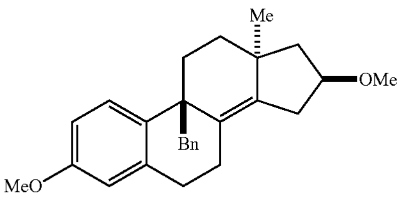 [SMILES: COc1ccc2c(c1)CCC1=C3C[C@H](OC)C[C@]3(C)CC[C@]12Cc1ccccc1] |
TABLE C-continued
| Compound | Structure |
|---|---|
| 302 | 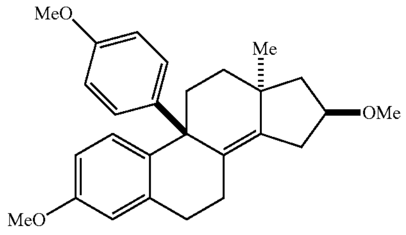 [SMILES: COc1ccc([C@@]23CC[C@@]4(C)C[C@@H](OC)CC4=C2CCc2cc(OC)ccc23)cc1] |
| 303 | 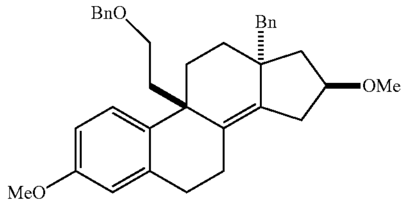 [SMILES: COc1ccc2c(c1)CCC1=C3C[C@H](OC)C[C@]3(Cc3ccccc3)CC[C@]12CCOCc1ccccc1] |
| 304 | 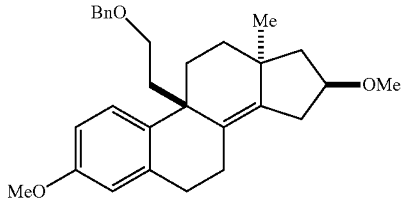 [SMILES: COc1ccc2c(c1)CCC1=C3C[C@H](OC)C[C@]3(C)CC[C@]12CCOCc1ccccc1] |
| 305 | 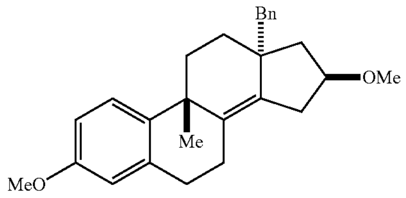 |
| 306 | 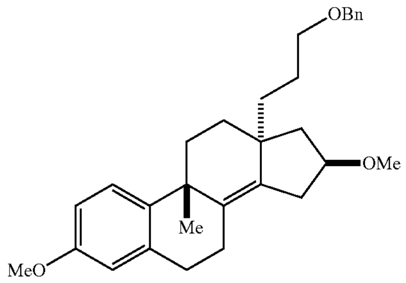 |
| 307 | 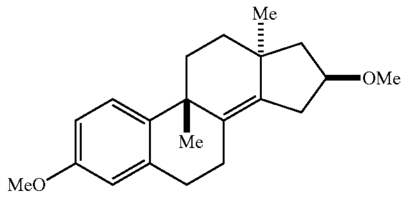 |
| 308 | 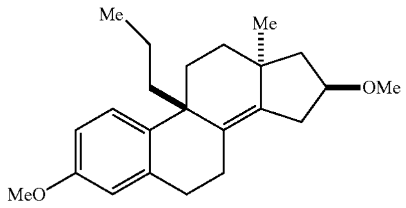 [SMILES: CCC[C@@]12CC[C@@]3(C)C[C@@H](OC)CC3=C1CCc1cc(OC)ccc12] |

TABLE C-continued

| Compound | Structure |
| --- | --- |
| 309 | 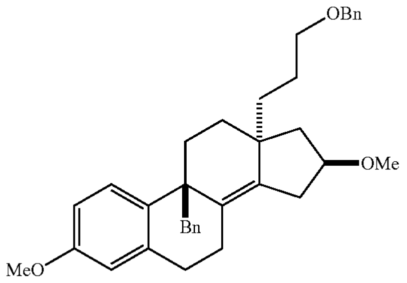 [SMILES: COc1ccc2c(c1)CCC1=C3C[C@H](OC)C[C@]3(CCCOCc3ccccc3)CC[C@]12Cc1ccccc1] |

D. Methods of Use

In at least one aspect, the present disclosure includes a method for treating or preventing a glucocorticoid-dependent condition in a subject in need of such treatment or prevention. In certain embodiments, the glucocorticoid-dependent condition is a proliferative disease. Exemplary proliferative diseases include cancers (i.e., "malignant neoplasms"). In particular, exemplary proliferative diseases that may be treated or prevented include prostate cancer. In certain embodiments, the glucocorticoid-dependent condition is cancer (e.g., prostate cancer), hypercortisolism, a mood affective disorder such as a depressive disorder (e.g., psychotic depression), a neurodegenerative disease (e.g., Alzheimer's disease), neuropathic pain, diabetes, or glaucoma.

Thus, one aspect of the present disclosure includes a method for treating cancer. The method comprises administering to a patient in need thereof a therapeutically effective amount of a compound described herein (including, but not limited to, Compound 101 or Compound 102) or a pharmaceutically acceptable salt or prodrug thereof. In some embodiments, the compound is Compound 101. In some embodiments, the compound is Compound 102. In some embodiments, the compound (or pharmaceutically acceptable salt thereof) is administered orally. In some embodiments, the compound (or pharmaceutically acceptable salt thereof) is administered parenterally, such as intramuscularly, subcutaneously, or transdermally.

In at least one aspect, the present disclosure includes a compound disclosed herein or a pharmaceutically acceptable salt or prodrug thereof for use in a method for treating or preventing a glucocorticoid-dependent condition in a subject in need of such treatment or prevention. In certain embodiments, the glucocorticoid-dependent condition is a proliferative disease. Exemplary proliferative diseases include cancers (i.e., "malignant neoplasms"). In particular, exemplary proliferative diseases that may be treated or prevented include prostate cancer. In certain embodiments, the glucocorticoid-dependent condition is cancer (e.g., prostate cancer), hypercortisolism, a mood affective disorder such as a depressive disorder (e.g., psychotic depression), a neurodegenerative disease (e.g., Alzheimer's disease), neuropathic pain, diabetes, or glaucoma.

Thus, the present disclosure includes a compound disclosed herein or a pharmaceutically acceptable salt or prodrug thereof for use in a method for treating a cancer, particularly prostate cancer. In certain embodiments, the compound is Compound 101. In certain embodiments, the compound is Compound 102. In certain embodiments, Compound 101 or Compound 102 can be used in combination with one or more additional therapeutic agents.

In certain embodiments, the cancer is prostate cancer. In some such embodiments, Compound 101 or Compound 102 can be used in combination with one or more additional therapeutic agents such as an antiandrogen (e.g., enzalutamide). In certain embodiments, the prostate cancer is castration-resistant prostate cancer ("CRPC"), particularly metastatic CRPC.

In certain embodiments, the cancer is breast cancer, such as triple negative breast cancer.

In certain embodiments, the cancer is ovarian cancer, such as high grade serous ovarian cancer.

In certain embodiments, the cancer is lung cancer, such as non-small cell lung cancer.

Another aspect of the present disclosure includes a method for treating or preventing hypercortisolism in a subject in need of such treatment or prevention.

Still another aspect of the present disclosure includes a method for treating or preventing a mood affective disorder such as a depressive disorder (e.g., psychotic depression), a neurodegenerative disease (e.g., Alzheimer's disease), neuropathic pain, diabetes, or glaucoma in a subject in need of such treatment or prevention.

One aspect of the present disclosure includes a method for treating or preventing a disease or condition that is at least partially mediated or affected by a glucocorticoid receptor (GR) in a subject in need of such treatment or prevention.

Another aspect of the present disclosure includes a method for treating or preventing a disease or condition treatable or preventable by selectively modulating GR in a subject in need of such treatment or prevention.

In certain embodiments, for any of the aforementioned aspects, the subject is a mammal. In some such embodiments, the mammal is a human.

In certain embodiments, for any of the aforementioned aspects, the methods comprise administering to the subject a therapeutically effective amount of a compound described herein (including, but not limited to, Compound 101 or Compound 102) or a pharmaceutically acceptable salt or prodrug thereof as single agent or in combination with another therapeutic agent. In some such embodiments, the methods comprise administering to the subject a therapeutically effective amount of Compound 101 or a pharmaceutically acceptable salt or prodrug thereof, preferably Compound 101. In other such embodiments, the methods comprise administering to the subject a therapeutically effective amount of Compound 102 or a pharmaceutically acceptable salt or prodrug thereof, preferably Compound 102. In certain embodiments, the compound is administered orally.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). In certain embodiments, dosage unit compositions contain such amounts or submultiples thereof to make up the daily dose. In many instances, the administration of the compound or salt will be repeated a plurality of times. In certain embodiments, multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

The activity of a compound can be determined using various known methods. For example, GR assays can be used. Such GR assays include binding assays using, for example, cells transfected with the human glucocorticoid receptor (NR3C1). Several cell based model systems that allow sensitive detection and monitoring of steroids or other compounds with GR bioactivity are known. Most cell based GR reporter models use transgenic gene constructs that include a glucocorticoid response element (GRE) that controls reporter gene (e.g., lucifersrase) expression. For example, a human GR Reporter Assay System is commercially available from Indigo Biosciecnes. An exemplary assay system or test kit includes reporter cells including a reporter gene (e.g., lucifersrase) functionally linked to a GR-responsive promoter, a reference agonist (e.g., dexamethasone), and a reference antagonist (e.g., mifepristone). The principle application of such an assay product is to quantify functional activities, either agonist or antagonist, that a compound may exert against the human glucocorticoid receptor.

E. Compositions

In at least one aspect, the present disclosure includes compositions comprising a compound described herein (including, but not limited to, Compound 101 or Compound 102) or a pharmaceutically acceptable salt or prodrug thereof. In certain embodiments, the composition comprises one or more conventional pharmaceutically acceptable excipients.

In at least one aspect, the present disclosure includes compositions comprising an enantiomeric compound described herein. In certain embodiments, the composition is enantiomerically pure or enriched. For example, the composition may comprise at least 85% of one enantiomer and not more than 15% of the other enantiomer; alternatively, at least 90% of one enantiomer and not more than 10% of the other enantiomer; alternatively, at least 95% of one enantiomer and not more than 5% of the other enantiomer; alternatively, at least 97% of one enantiomer and not more than 3% of the other enantiomer; or alternatively, at least 99% of one enantiomer and not more than 1% of the other enantiomer. In certain embodiments, the composition is substantially free of enantiomeric impurities. In some such embodiments, the composition is free of any detectable amount of an enantiomeric impurity.

Pharmaceutical compositions disclosed herein comprise a compound disclosed herein or a pharmaceutically acceptable salt or prodrug thereof, preferably, Compound 101 or Compound 102. In some embodiments, the pharmaceutical composition is an oral dosage form, preferably a solid oral dosage form (e.g., a tablet). In some such embodiments, the solid oral dosage form may comprise pharmaceutically acceptable excipients such as excipients that function as binders, glidants, lubricants, and fillers. Thus, a solid oral dosage form comprising a compound disclosed herein or a pharmaceutically acceptable salt thereof further optionally comprises one or more conventional pharmaceutically acceptable excipients.

In some embodiments, a compound is co-administered with at least one additional therapeutic agent. In some such embodiments, the additional therapeutic agent is a non-steroidal antiandrogen (NSAA) medication, such as flutamide, nilutamide, bicalutamide, topilutamide, apalutamide, enzalutamide, darolutamide, proxalutamide, or seviteronel.

In some embodiments, the additional therapeutic agent and the compound of the present disclosure are co-administered to the patient in a substantially simultaneous manner (e.g., or within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some embodiments, the additional therapeutic agent and the compound of the present disclosure are administered in separate pharmaceutical compositions. In some embodiments, the additional therapeutic agent and the compound of the present disclosure are administered in the same pharmaceutical composition.

In at least one aspect, the present disclosure includes a pharmaceutical composition for treating a glucocorticoid-dependent condition such as cancer or hypercortisolism, the composition comprising a compound disclosed herein or a pharmaceutically acceptable salt thereof and a pharmaceutically acceptable excipient. In certain embodiments, the compound is Compound 101. In certain embodiments, the compound is Compound 102.

It will be readily apparent to those skilled in the art that other suitable modifications and adaptations of the compositions and methods of the invention described herein may be made using suitable equivalents without departing from the scope of the invention or the embodiments disclosed herein.

The compounds, compositions, and methods described herein will be better understood by reference to the following examples, which are included as an illustration of and not a limitation upon the scope of the invention.

F. EXAMPLES

Example 1. Synthesis of Compounds 101 and 102

Compound A—(9S,13S,16R)-9-benzyl-16-hydroxy-13-methyl-N-(2-methylpyridin-3-yl)-7,9,11,12,13,15,16,17-octahydro-6H-cyclopenta[α]phenanthrene-3-carboxamide Compound 101—(9S,13S,16R)-9-benzyl-13-methyl-3-(2-methylpyridin-3-yl)-7,9,11,12,13,15,16,17-octahydro-6H-cyclopenta[α]phenanthren-16-ol Compound 102—(9S,13S,16R)-9-benzyl-13-methyl-3-((2-methylpyridin-3-yl)amino)-7,9,11,12,13,15,16,17-octahydro-6H-cyclopenta[α]phenanthren-16-ol The above compounds were prepared in 4 steps from Enyne 1, which is available from, for example, epichlorohydrin.

Preparation of Compounds A, 101, and 102 from Enyne 1:

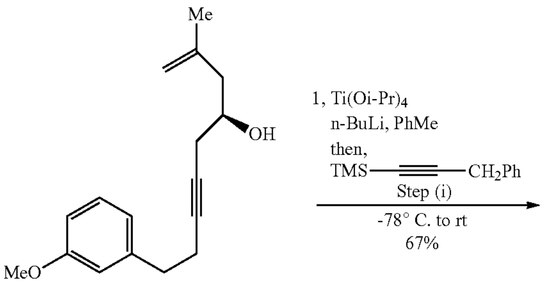

Enyne 1

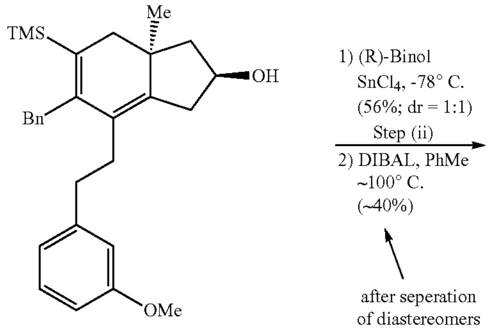

Hydrindane 1

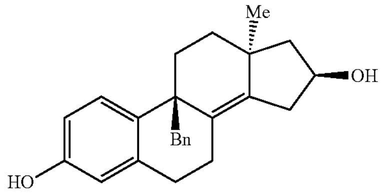

Intermediate Tetracycle 1

The first step was a titanium-mediated annulation reaction as generally described above to provide the stereodefined Hydrindane 1.

In the second step, Hydrindane 1, which is a silyl-substituted diene, was reacted with (R)-Binol and $SnCl_4$ at −78° C. and subsequently with DIBAL and PhMe at 100° C. to deliver Intermediate Tetracycle 1.

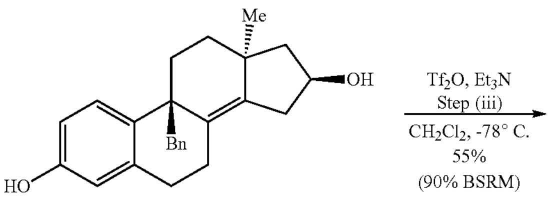

Intermediate Tetracycle 1

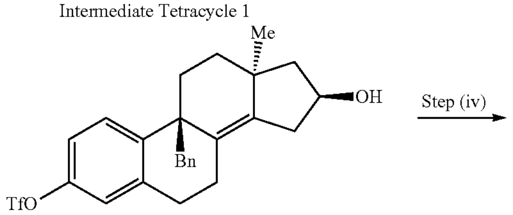

-continued

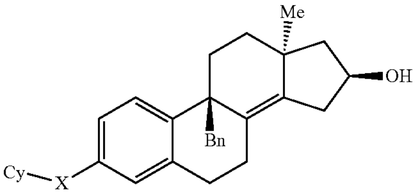

In the third step, the intermediate tetracyclic product was reacted with $Tf_2O$, $Et_3N$, and $CH_2Cl_2$ at −78° C.

The fourth step comprised different functionalization at C3. For Compound A, the fourth step comprised a Pd-catalyzed carbonylation and amination. For Compound 101, the fourth step comprised a Suzuki coupling reaction. For Compound 102, the fourth step comprised a Pd-catalyzed C—N bond formation.

Example 2. Activity of Compounds 101 and 102

The activity of certain compounds were tested in a human GR antagonist assay (Indigo Biosciences).

Compound A was not active. Compound 101 had an $IC_{50}$<100 nm. Compound 102 had an $IC_{50}$ of 16 nM.

Results from the human GR antagonist assay are shown in FIG. 1 and Table 1.

TABLE 1

| | Mifepristone | Compound A | Compound 101 | Compound 102 |
|---|---|---|---|---|
| HillSlope | 0.8706 | No activity | Cannot be determined | 1.042 |
| IC50 (nM) | 1.139 | | | 16.40 |

Example 3. Stereoselection for C9-C10 Bond Formation with Aromatic Groups at C9; Synthesis of Compound 301

When proceeding in a manner similar to Example 1, low levels of stereoselectivity were observed when the group at C9 is aromatic, particularly benzyl (Bn).

For example, starting from Hydrindane 1 of Example 1, the following reaction resulted in a relatively low level of stereoselectivity:

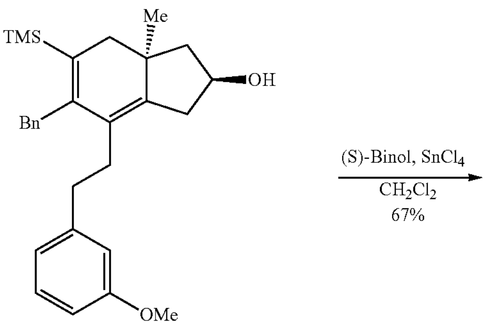

Hydrindane 1

-continued

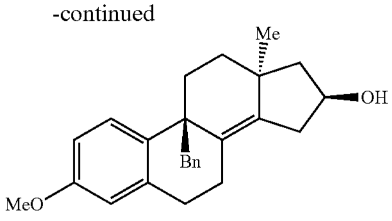

d.s. = 2:1

Desilylation of Hydrindane 1 at C11 did not improve steresoselectivity:

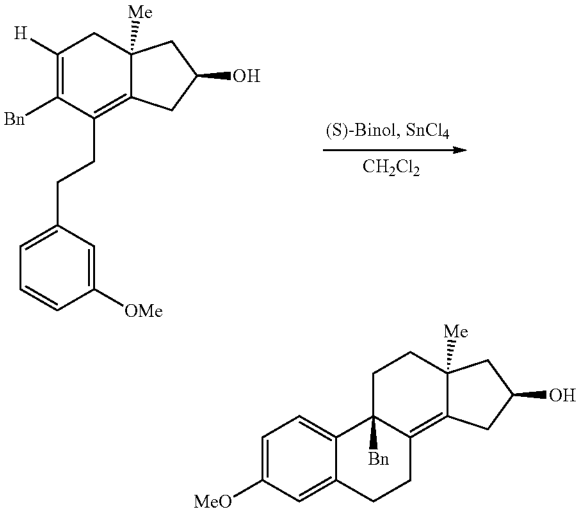

d.s. = 2:1

Protection of the free hydroxy group (at C16) of Hydrindane 1 slightly improved stereoselectivity:

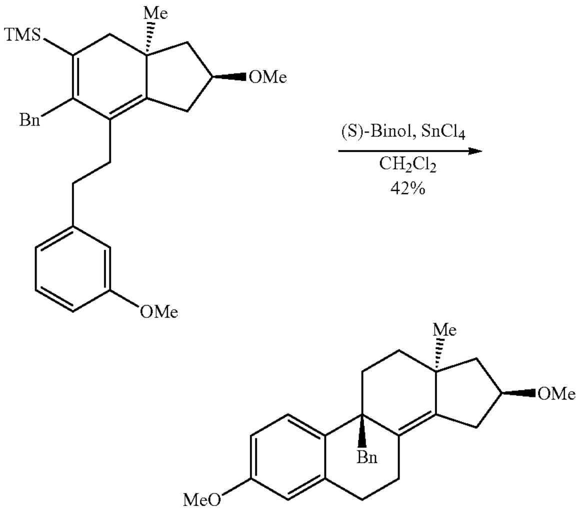

Compound 201
d.s. = 6:1

Desilylation of Hydrindane 1 at C11 and protection of the free hydroxy group (at C16) dramatically improved stereoselectivity:

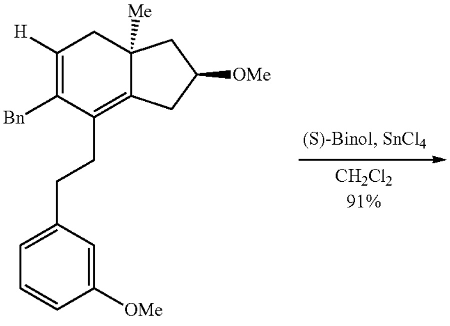

Compound 201

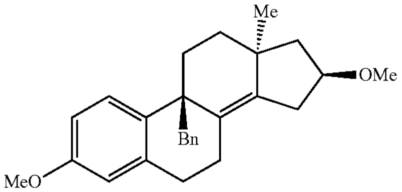

Compound 301
d.s. > 20:1

Hydroxy group protection and protodesilylation unexpectedly achieved high levels of stereoselection in Brønsted acid-mediated regio- and stereoselective Friedel-Crafts cyclization reaction to generate the steroidal C9-C10 bond.

Example 4. Synthesis of Compounds 302-304

This Example further established that the synthetic methods disclosed herein can be used to prepare compounds having an aromatic moiety attached at C9.

Compound 302—(9S,13S,16R)-3,16-dimethoxy-9-(4-methoxyphenyl)-13-methyl-7,9,11,12,13,15,16,17-octahydro-6H-cyclopenta[α]phenanthrene

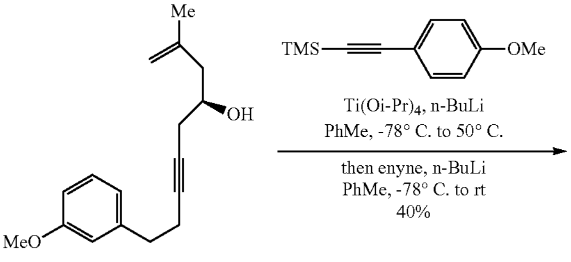

Enyne 1

-continued

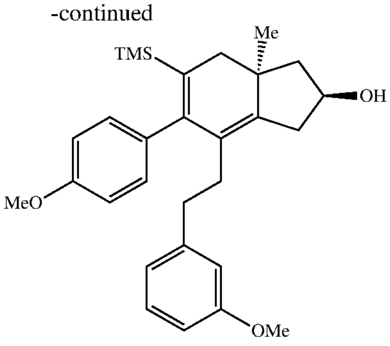

Hydrindane 2

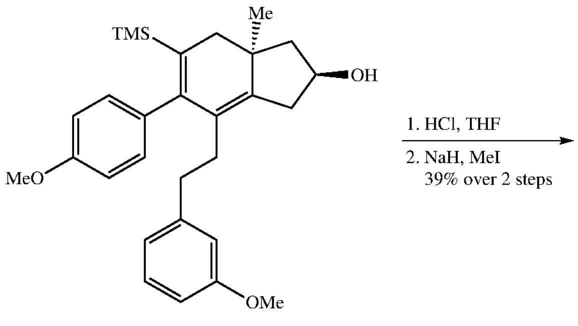

Hydrindane 2

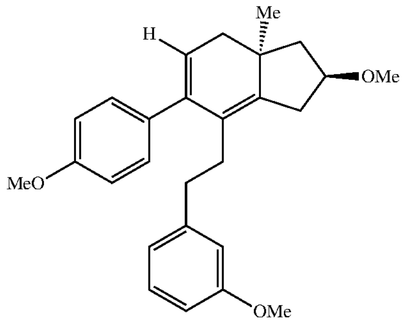

Compound 202

Synthesis of Hydrindane 2: To a stirred solution of TMS-alkyne (652 mg, 3.19 mmol, 3.3 equiv), $Ti(Oi\text{-}Pr)_4$ (0.944 mL, 3.19 mmol, 3.3 equiv), and PhMe (10.6 mL) at −78° C. in a 50 mL round-bottom flask was added n-BuLi (2.5 mL, 6.28 mmol, 6.4 equiv, 2.5 M in hexanes). The solution was allowed to warm to rt, and then heated to 50° C. for 1 h. Following this, the solution was then cooled to rt. At the same time, to enyne (250 mg, 0.967 mmol, 1.0 equiv) in PhMe (3.2 mL) in a 10 mL round-bottom flask at −78° C. was added n-BuLi (2.42 mL, 0.967 mmol, 1.0 equiv, 2.5 M in hexanes). Following the dropwise addition, the solution was allowed to warm to rt. At rt, the flask containing the enyne was added dropwise to the flask containing the TMS-alkyne. The solution was stirred overnight before the addition of benzaldehyde (3.19 mmol, 3.3 equiv), which was stirred for 30 min before the addition of sat. aq. $NaHCO_3$ (8 mL). The biphasic solution was stirred for 30 min before the phases were separated, and the aqueous phase was extracted with EtOAc (3×30 mL). The combined organic phase was dried over $Na_2SO_4$, filtered, and concentrated in vacuo. The resulting crude oil was purified by flash chromatography with a Biotage® Snap Ultra 25 g cartridge and a gradient from 0-40% EtOAc in hexanes to afford Hydrindane 2 (180 mg, 0.389 mmol, 40%) as a pale, yellow oil.

Data for compound Hydrindane 2: TLC: $R_f$=0.24 (20% EtOAc in hexanes); $^1$H NMR (600 MHz, $CDCl_3$): δ 7.16 (s, 2H), 6.99 (t, J=7.90 Hz, 1H), 6.85 (s, 1H), 6.75 (s, 2H), 6.57 (d, J=7.90 Hz, 1H), 6.41 (d, J=7.50 Hz, 1H), 6.27 (s, 1H), 4.35 (p, J=6.94 Hz, 1H), 3.72 (s, 3H), 3.63 (s, 3H), 2.59 (dd, J=7.67 Hz, 1H), 2.26-2.21 (m, 2H), 2.15-2.07 (m, 2H), 2.01 (m, 3H), 1.95-1.90 (m, 1H), 1.38 (q, J=4.50 Hz, 1H), 0.84 (s, 3H), −0.33 (s, 9H) δ; $^{13}$C NMR (150 MHz, $CDCl_3$): 159.38, 158.47, 147.37, 144.58, 143.91, 134.67, 131.67, 128.98, 128.62, 120.98, 114.09, 111.10, 71.95, 55.22, 55.06, 51.09, 41.08, 39.49, 38.29, 35.30, 32.31, 21.31, 21.15, 0.62 δ; IR (neat, $cm^{-1}$): 3366 (s), 2950 (m), 1652 (m), 1608 (m), 1584 (w), 1540 (m), 1505 (m), 1488 (m), 1456 (m), 1363 (w), 1245 (w), 1170 (s), 1151 (m), 1038 (m), 835 (s), HRMS (ESI-TOF) (m/z): $[M+H]^+$ calcd for $C_{29}H_{39}O_3Si$ 463.2668; found, 463.2651;

$[\alpha]^{21.6}_{589}$:

50.2299 (c 0.145, $CHCl_3$).

Synthesis of Compound 202: To a stirred solution of Hydrindane 2 (87 mg, 0.188 mmol, 1.0 equiv) at 0° C. in THF (1 mL) was slowly added 2M HCl (2 mL). The reaction mixture was allowed to slowly warm to rt over 4 h. Once reaction was complete by TLC the mixture was cooled to 0° C. and quenched with a saturated aqueous solution of $NaHCO_3$ (3 mL), followed by dilution with EtOAc (5 mL), the biphasic solution was separated, and the aqueous phase was extracted with EtOAc (3×10 mL). The combined organic phases were dried over $MgSO_4$, filtered, and concentrated in vacuo. The resulting crude oil was purified by flash chromatography with a Biotage® Snap Ultra 25 g cartridge and a gradient from 0-15% EtOAc in hexanes to afford the desilylated hydrindane as a clear oil which was immediately used in the next reaction.

To a stirred solution of desilylated hydrindane (43 mg, 0.110 mmol, 1.0 equiv) in THF (2 mL) at 0° C. was added NaH (13.2 mg, 0.330 mmol, 3 equiv), and the solution was stirred for 10 min before the addition of MeI (0.041 mL, 0.660 mmol, 6 equiv). The solution was allowed to warm to rt and stirred overnight. Upon completion, the reaction was quenched with $H_2O$ (3 mL), the phases were separated, and the aqueous phase was extracted with EtOAc (3×10 mL). The combined organic phase was dried over $Na_2SO_4$, filtered, and concentrated in vacuo. The resulting crude oil was purified by flash chromatography with a Biotage® Sfär 25 g cartridge and a gradient from 0-15% EtOAc in hexanes to afford Compound 202 (16 mg, 0.046 mmol, 39% over two steps).

Data for Compound 202: TLC: $R_f$=0.43 (20% EtOAc in hexanes); $^1$H NMR (600 MHz, $CDCl_3$): δ 7.14 (d, J=8.40, 2H), 7.08 (t, J=7.73, 1H), 6.87 (d, J=8.30 Hz, 2H), 6.66 (dd, J=2.61 Hz, 1H), 6.49 (d, 7.52 Hz, 1H), 6.34 (s, 1H), 5.61 (t, J=4.60 Hz, 1H), 4.04 (q, 7.60 Hz, 1H), 3.82 (s, 3H), 3.71 (s, 3H), 3.34 (s, 3H), 2.82 (dd, J=7.86 Hz, 1H), 2.36-2.22 (m, 6H), 2.18 (dd, J=7.40 Hz, 1H), 2.12 (dd, 6.11 Hz, 1H), 1.46 (t, J=10.48 Hz, 1H), 0.99 (s, 3H) δ; $^{13}$C NMR (150 MHz, $CDCl_3$): 159.33, 158.36, 143.84, 143.41, 139.53, 134.09, 129.14, 128.96, 126.88, 122.83, 120.79, 113.92, 113.30, 111.10, 80.21, 56.85, 55.24, 55.03, 47.52, 39.66, 37.76, 34.92, 34.70, 32.38, 22.23 δ; IR (neat, $cm^{-1}$): 2923 (m), 1609 (m), 1509 (w), 1454 (m), 1244 (m), 1173(s), 1108 (m), 1038 (m), 836 (s), 697 (s), HRMS (ESI-TOF) (m/z): $[M+H]^+$ calcd for $C_{27}H_{33}O_3$ 405.2430; found, 405.2427;

$[\alpha]^{21.7}_{589}$:

24.82 (c 0.145, $CHCl_3$).

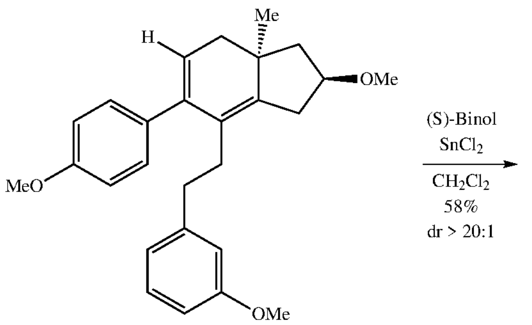

Compound 202

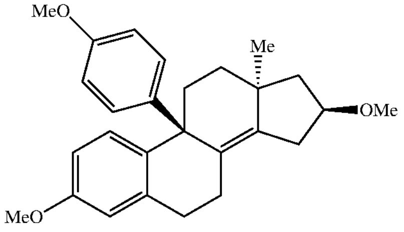

Compound 302

Synthesis of Compound 302: To a stirred solution of (S)-BINOL (10 mg, 0.034 mmol, 1.1 equiv) in $CH_2Cl_2$ (1 mL) at −78° C. was added $SnCl_4$ (0.031 mL, 0.031 mmol, 1.0 equiv, 1.0 M in $CH_2Cl_2$) which was stirred for 30 min at that temperature before the addition of Compound 202 (12.5 mg, 0.031 mmol, 1.0 equiv) in $CH_2Cl_2$ (1 mL), and the solution was kept at that temperature for 1 h before being allowed to warm to rt. After 1 h, the reaction mixture was quenched with sat. aq. $NH_4Cl$ (2 mL). The biphasic solution was stirred for 1 h before being transferred to a separatory funnel where the phases were separated, and the aqueous phase was extracted with $CH_2Cl_2$ (3×5 mL). The combined organic phase was washed with 3M NaOH (3 mL), was dried over $MgSO_4$, filtered, and concentrated in vacuo. The resulting crude product was purified by flash chromatography with a Biotage® Snap Ultra 25 g column and a gradient from 0-15% EtOAc in hexanes additive to afford Compound 302 (7.2 mg, 0.018 mmol, 58%) as a white foam.

Data for Compound 302: TLC: $R_f$=0.40 (20% EtOAc in hexanes); $^1H$ NMR (600 MHz, $CDCl_3$): δ 7.54 (d, J=8.46 Hz, 1H), 6.94 (d, 8.46 Hz, 2H), 6.84 (dd, J=8.44 Hz, 1H), 6.71 (d, J=8.46 Hz, 2H), 6.64 (s, 1H), 4.18 (q, J=6.05 Hz, 1H), 3.80 (s, 3H), 3.74 (s, 3H), 3.39 (s, 3H), 2.73 (dd, J=8.72 Hz, 1H), 2.51 (dd, J=7.11 Hz, 1H), 2.44-2.41 (m, 2H), 2.36 (dd, J=4.77 Hz, 1H), 2.25-2.10 (m, 3H), 2.07 (d, J=12.88 Hz, 1H), 1.50 (m, 2H), 1.40 (t, J=10.11 Hz, 1H), 0.96 (s, 3H) δ; $^{13}C$ NMR (150 MHz, $CDCl_3$): 157.80, 157.38, 140.55, 139.80, 139.35, 137.70, 128.61, 113.61, 112.91, 110.68, 80.14, 56.95, 55.18, 55.12, 48.48, 47.12, 41.33, 34.60, 47.12, 41.33, 34.60, 31.29, 28.21, 26.78, 25.61 δ; IR (neat, $cm^{-1}$): 2926 (m), 1733 (s), 1717 (m), 1698 (m), 1606 (w), 1577 (m), 1558 (m), 1506 (m), 1456 (m), 1373 (w), 1246 (w), 1176 (s), 1102 (m), 1040 (m), 829 (s), HRMS (ESI-TOF) (m/z): $[M+H]^+$ calcd for $C_{27}H_{33}O_3$ 405.2430; found, 405.2418;

$[\alpha]^{21.8}_{589}$:

103.715 (c 0.15, $CHCl_3$).

Compounds 303-304 were prepared in a similar manner:

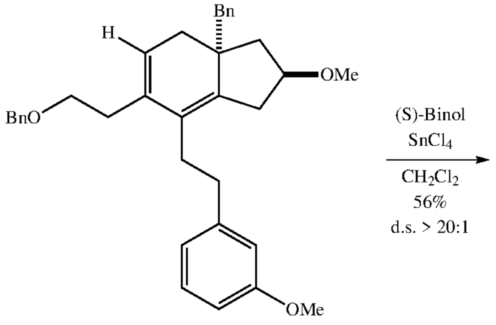

Compound 203

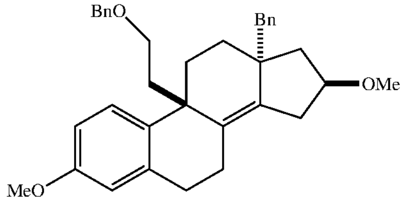

Compound 303

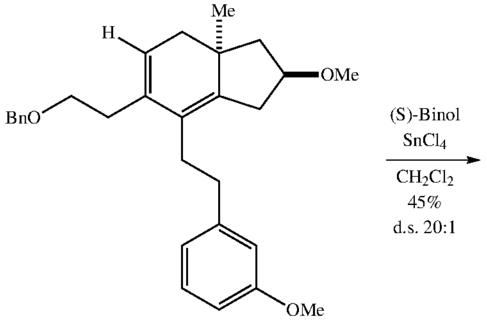

Compound 204

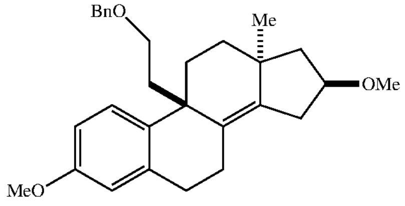

Compound 304

Example 5. Synthesis of Compounds 305-307

This Example established that the synthetic methods disclosed herein were effective for a variety of substrates, including those with alkyl substituents at C9.

5A. Compound 305—(9R,13R,16R)-13-benzyl-3,16-dimethoxy-9-methyl-7,9,11,12,13,15,16,17-octahydro-6H-cyclopenta[α]phenanthrene

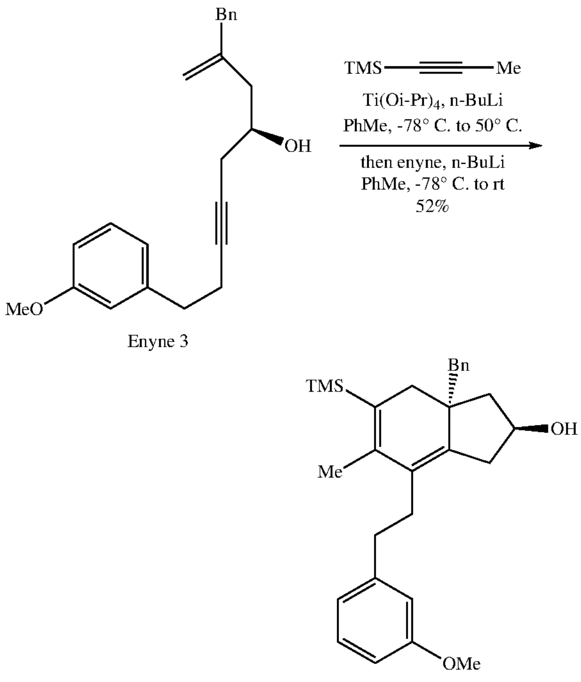

Enyne 3

Hydrindane 3

Synthesis of Hydrindane 3: To a stirred solution of TMS-propyne (0.333 mL, 2.25 mmol, 3.3 equiv), $Ti(Oi\text{-}Pr)_4$ (0.666 mL, 2.25 mmol, 3.3 equiv), and PhMe (7.5 mL) at −78° C. in a 50 mL round-bottom flask was added n-BuLi (1.95 mL, 4.875 mmol, 6.4 equiv, 2.5 M in hexanes). The solution was allowed to warm to rt, and then heated to 50° C. for 1 h. Following this, the solution was then cooled to rt. At the same time, to enyne (250 mg, 0.75 mmol, 1.0 equiv) in PhMe (2.5 mL) in a 10 mL round-bottom flask at −78° C. was added n-BuLi (0.3 mL, 0.967 mmol, 1.0 equiv, 2.5 M in hexanes). Following the dropwise addition, the solution was allowed to warm to rt. At rt, the flask containing the enyne was added dropwise to the flask containing the TMS-alkyne. The solution was stirred overnight before the addition of benzaldehyde (0.75 mmol, 3.3 equiv), which was stirred for 30 min before the addition of sat. aq. $NaHCO_3$ (8 mL). The biphasic solution was stirred for 30 min before the phases were separated, and the aqueous phase was extracted with EtOAc (3×30 mL). The combined organic phase was dried over $Na_2SO_4$, filtered, and concentrated in vacuo. The resulting crude oil was purified by flash chromatography with a Biotage® Snap Ultra 25 g cartridge and a gradient from 0-40% EtOAc in hexanes to afford Hydrindane 3 (176 mg, 0.394 mmol, 52%) as a pale, yellow oil.

Data for Hydrindane 3: TLC: $R_f$=0.24 (20% EtOAc in hexanes); $^1$H NMR (600 MHz, $CDCl_3$): δ 7.24 (t, J=7.42 Hz, 2H), 7.19 (dq, J=3.95 Hz, 2H), 7.05 (d, J=7.41 Hz, 2H), 6.75 (dd, J=7.47, 8.17 Hz, 2H), 6.70 (s, 1H), 4.09 (t, J=6.50 Hz, 1H), 3.79 (s, 3H), 2.69 (m, 1H), 2.56 (m, 3H), 2.37 (m, 3H), 2.28 (m, 2H), 2.03 (s, 2H), 1.96 (dd, J=5.34, 17. 43 Hz, 2H), 1.88 (d, J=16.69 Hz, 1H), 1.21 (dd, J=6.93, 6.07 Hz, 1H), δ; $^{13}$C NMR (150 MHz, $CDCl_3$): 159.51, 143.84, 143.63, 142.11, 139.18, 130.25, 130.07, 129.19, 128.90, 127.75, 125.92, 121.11, 114.71, 110.94, 71.68, 55.13, 47.28, 44.35, 39.45, 39.23, 38.51, 35.58, 31.59, 19.28, 0.27 δ; IR (neat, $cm^{-1}$): 3349 (s), 2948 (m), 1601 (m), 1491 (s), 1453 (m), 1259 (m), 1152 (m), 1053 (m), 835 (m), 741(m), 703 (s) HRMS (ESI-TOF) (m/z): $[M+Na]^+$ calcd for $C_{29}H_{33}O_2SiNa$ 469.2641; found, 469.2531;

$[\alpha]^{20.8}_{589}$:

−100.55 (c 0.51, $CHCl_3$).

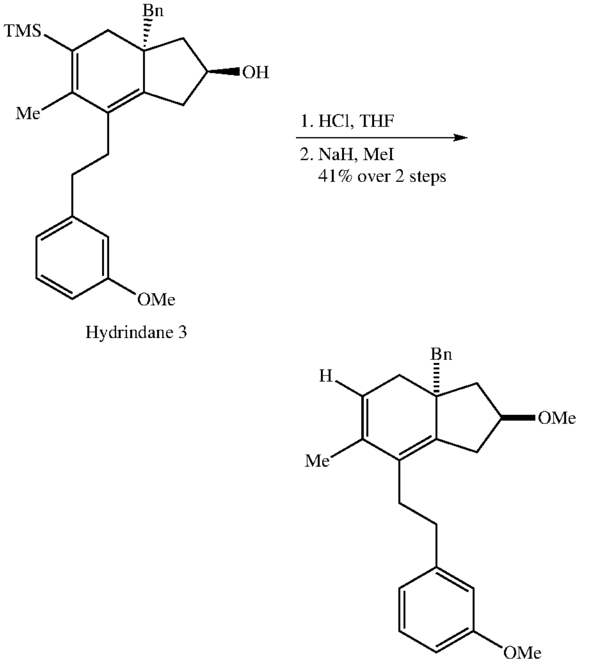

Hydrindane 3

Compound 205

Synthesis of Compound 205: To a stirred solution of Hydrindane 3 (284 mg, 0.636 mmol, 1.0 equiv) at 0° C. in THF (4 mL) was slowly added 1M HCl (3 mL). The reaction mixture was allowed to slowly warm to rt over 4 h. Once reaction was complete by TLC the mixture was cooled to 0° C. and quenched with a saturated aqueous solution of $NaHCO_3$ (5 mL), followed by dilution with EtOAc (7 mL), the biphasic solution was separated, and the aqueous phase was extracted with EtOAc (3×20 mL). The combined organic phases were dried over $MgSO_4$, filtered, and concentrated in vacuo. The resulting crude oil was purified by flash chromatography with a Biotage® Snap Ultra 25 g cartridge and a gradient from 0-15% EtOAc in hexanes to afford desilylated hydrindane as a clear oil which was immediately used in the next reaction.

To a stirred solution of desilylated hydrindane (142 mg, 0.340 mmol, 1.0 equiv) in THF (2 mL) at 0° C. was added NaH (41 mg, 1.02 mmol, 3 equiv), and the solution was stirred for 10 min before the addition of MeI (0.127 mL, 2.04 mmol, 6 equiv). The solution was allowed to warm to rt and stirred overnight. Upon completion, the reaction was quenched with $H_2O$ (3 mL), the phases were separated, and the aqueous phase was extracted with EtOAc (3×15 mL). The combined organic phase was dried over $Na_2SO_4$, filtered, and concentrated in vacuo. The resulting crude oil was purified by flash chromatography with a Biotage® Sfär 25 g cartridge and a gradient from 0-15% EtOAc in hexanes to afford Compound 205 (100 mg, 0.257 mmol, 41% over two steps).

Data for Compound 205: TLC: $R_f$=0.43 (20% EtOAc in hexanes); $^1H$ NMR (600 MHz, $CDCl_3$): δ 7.27 (t, J=7.72 Hz, 2H), 7.20 (t, J=7.72 Hz, 2H), 7.09 (d, J=7.41 Hz, 2H), 6.80 (d, J=7.41 Hz, 1H), 6.75 (m, 2H), 5.50 (d, J=5.89 Hz, 1H), 3.88 (p, J=7.42 Hz, 1H), 3.80 (s, 3H), 3.27 (s, 3H), 2.65-2.56 (m, 4H), 2.45-2.36 (m, 3H), 2.30 (dd, J=6.58, 5.99 Hz, 1H), 2.14 (dd, J=6.28, 17.76 Hz, 2H), 1.91 (s, 1H), 1.89 (s, 3H), 1.19 (dd, J=3.91, 10.67 Hz, 1H), δ; $^{13}C$ NMR (150 MHz, $CDCl_3$): 157.80, 157.38, 140.55, 139.80, 139.35, 137.70, 128.61, 113.61, 112.91, 110.68, 80.14, 56.95, 55.18, 55.12, 48.48, 47.12, 41.33, 34.60, 47.12, 41.33, 34.60, 31.29, 28.21, 26.78, 25.61 δ; IR (neat, $cm^{-1}$): 2926 (m), 1733 (s), 1717 (m), 1698 (m), 1606 (w), 1577 (m), 1558 (m), 1506 (m), 1456 (m), 1373 (w), 1246 (w), 1176 (s), 1102 (m), 1040 (m), 829 (s), HRMS (ESI-TOF) (m/z): $[M+H]^+$ calcd for $C_{27}H_{33}O_3$ 389.2481; found, 389.2465;

$[\alpha]^{21.8}_{589}$:

103.715 (c 0.15, $CHCl_3$).

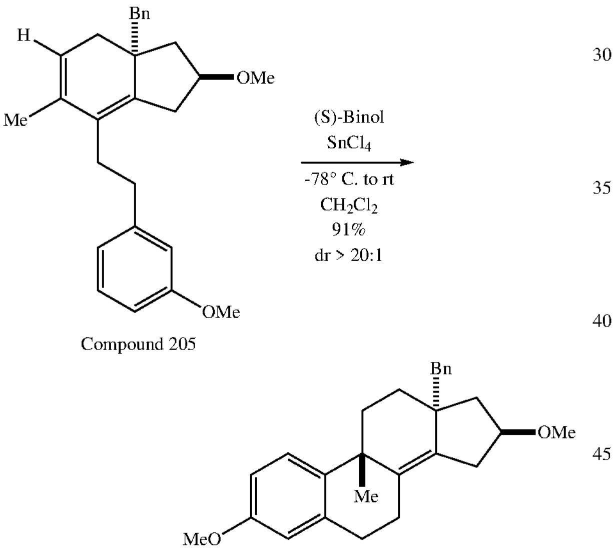

Compound 205

Compound 305

Synthesis of Compound 305: To a stirred solution of (S)-BINOL (37 mg, 0.127 mmol, 1.1 equiv) in $CH_2Cl_2$ (1 mL) at −78° C. was added $SnCl_4$ (0.116 mL, 0.116 mmol, 1.0 equiv, 1.0 M in $CH_2Cl_2$) which was stirred for 30 min at that temperature before the addition of Compound 205 (45 mg, 0.116 mmol, 1.0 equiv) in $CH_2Cl_2$ (1 mL), and the solution was kept at that temperature for 1 h before being allowed to warm to rt. After 1 h, the reaction mixture was quenched with sat. aq. $NH_4Cl$ (2 mL). The biphasic solution was stirred for 1 h before being transferred to a separatory funnel where the phases were separated, and the aqueous phase was extracted with $CH_2Cl_2$ (3×5 mL). The combined organic phase was washed with 3M NaOH (3 mL), was dried over $MgSO_4$, filtered, and concentrated in vacuo. The resulting crude product was purified by flash chromatography with a Biotage® Snap Ultra 25 g column and a gradient from 0-15% EtOAc in hexanes additive to afford Compound 305 (41 mg, 0.105 mmol, 91%) as a white foam.

Data for Compound 305: TLC: $R_f$=0.40 (20% EtOAc in hexanes); $^1H$ NMR (600 MHz, $CDCl_3$): δ 7.25 (m, 3H), 7.20 (t, J=7.13 Hz, 1H), 7.08 (d, J=7.47 Hz, 2H), 6.79 (d, J=8.41 Hz, 1H), 6.62 (s, 1H), 4.21 (p, J=8.80, 5.19 Hz, 1H), 3.80 (s, 3H), 3.35 (s, 3H), 2.93 (dd, J=4.89, 16.55 Hz, 1H), 2.79 (m, 2H), 2.56 (d, J=13.56 Hz, 1H), 2.48 (dd, J=5.22, 14.04 Hz, 1H), 2.38 (m, 4H), 2.10 (d, J=13.22 Hz, 1H), 2.01 (t, J=13.59 Hz, 1H), 1.89 (d, J=13.65 Hz, 1H), 1.44 (t, J=13.25 Hz, 1H), 1.34 (s, 3H), 1.09 (dd, J=3.91, 8.53 Hz, 1H), δ; $^{13}C$ NMR (150 MHz, $CDCl_3$): 157.01, 139.96, 139.00, 137.14, 136.11, 132.78, 130.39, 127.89, 127.12, 126.01, 112.95, 112.42, 79.97, 56.83, 55.13, 45.47, 43.91, 41.16, 38.16, 34.49, 33.82, 32.24, 31.56, 28.70, 25.03, δ; IR (neat, $cm^{-1}$): 3025 (m), 2929 (m), 1607 (s), 1574 (s), 1497 (m), 1454 (m), 1368 (s). 1229 (m), 1037 (m), 968 (m), HRMS (ESI-TOF) (m/z): $[M+H]^+$ calcd for $C_{27}H_{33}O_2$ 389.2481; found, 389.2480;

$[\alpha]^{21.0}_{589}$:

−70.82 (c 1.495, $CHCl_3$).

5B. Compound 306—(9R,13R,16R)-13-(3-(benzyloxy)propyl)-3,16-dimethoxy-9-methyl-7,9,11,12,13,15,16,17-octahydro-6H-cyclopenta[α]phenanthrene

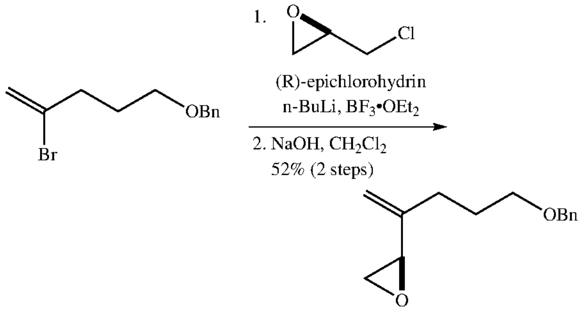

Synthesis of Epoxide: To a stirred solution of vinyl bromide (5.00 g, 19.6 mmol, 1.0 equiv) in THF (70 mL) at −78° C. in a 200 mL round-bottom flask was added n-BuLi (11.8 mL, 29.4 mmol, 1.5 equiv, 2.5 M in hexanes). The solution was stirred for 30 min before the addition of $BF_3 \cdot OEt_2$ (2.67 mL, 21.6 mmol, 1.1 equiv) then (R)-epichlorohydrin (1.69 mL, 21.6 mmol, 1.10 equiv) as a solution in THF (8 mL). The solution was stirred at −78° C. for 5 min before being warmed to rt where it was stirred for 1 h before being quenched with sat. aq. $NH_4Cl$ (20 mL). The phases were separated, the aqueous phase was extracted with EtOAc (3×30 mL), and the combined organic phase was dried over $Na_2SO_4$, filtered, and concentrated in vacuo. The resulting crude material was carried on directly to the next step without purification.

To the resulting crude material was added $CH_2Cl_2$ (40 mL) and NaOH (1.57 g, 39.2 mmol, 2.0 equiv) and the solution was stirred at rt overnight. Upon completion, the reaction was quenched with $H_2O$ (20 mL) and the phases were separated. The aqueous phase was extracted with $CH_2Cl_2$ (3×20 mL), and the combined organic phase was dried over $Na_2SO_4$, filtered through celite, and concentrated in vacuo. The resulting crude oil was purified by flash chromatography with a Biotage® Sfär 50 g cartridge and a gradient from 5-35% EtOAc in hexanes to afford epoxide (2.34 g, 10.1 mmol, 52%) as a pale, yellow oil.

Data for Epoxide: TLC: $R_f$=0.38 (20% EtOAc in hexanes); $^1$H NMR (600 MHz, $CDCl_3$): δ; 7.36-7.32 (m, 4H), 7.30-7.27 (m, 1H), 4.90 (s, 1H), 4.86 (s, 1H), 4.50 (d, J=2.4 Hz, 2H), 3.49 (td, J=6.4, 2.1 Hz, 2H), 3.05-3.00 (m, 1H), 2.79 (q, J=3.7 Hz, 1H), 2.51-2.47 (m, 1H), 2.31-2.25 (m, 1H), 2.23-2.14 (m, 3H), 1.81-1.75 (m, 2H); $^{13}$C NMR (150 MHz, $CDCl_3$): 145.4, 138.7, 128.5, 127.8, 127.7, 111.5, 73.1, 69.9, 51.3, 47.1, 39.4, 33.2, 27.9; IR (neat, $cm^{-1}$): 3031 (m), 2987 (m), 2923 (s), 2855 (s), 1646 (m), 1496 (w), 1454 (m), 1404 (w), 1363 (m), 1204 (w), 1104 (s), 1028 (w), 972 (w), 897 (m), 851 (m), 826 (m), 738 (m), 698 (s), 414 (s); HRMS (ESI-TOF) (m/z): $[M+H]^+$ calcd for; found;

$$[\alpha]^{22.1}_{589}:$$

+7.678 (c 0.0023, $CHCl_3$).

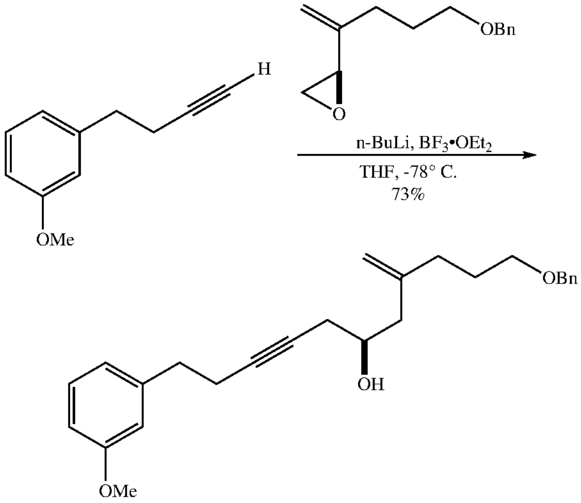

Enyne 4

Synthesis of Enyne 4: To a stirred solution of alkyne (4.05 g, 25.3 mmol, 2.5 equiv) in THF (70 mL) in a 200 mL round-bottom flask was added n-BuLi (6.10 mL, 15.2 mmol, 1.5 equiv, 2.5 M in hexanes). The solution was stirred for 30 min before the addition of $BF_3 \cdot OEt_2$ (2.54 mL, 20.2 mmol, 2.0 equiv), and after 30 more min ABM-5-126 (2.34 g, 10.1 mmol, 1.0 equiv) was added as a solution in THF (10 mL). The solution was stirred at −78° C. for 45 min before being quenched with sat. aq. $NaHCO_3$ (20 mL) and then warmed to rt. The solution was diluted with EtOAc (30 mL) and the phases were separated. The aqueous phase was extracted with EtOAc (3×30 mL) and the combined organic phases were dried over $Na_2SO_4$, filtered, and concentrated in vacuo. The resulting crude oil was purified by flash chromatography with a gradient from 5-35% EtOAc in hexanes to afford Enyne 4 (2.88 g, 7.34 mmol, 73%) as an orange oil.

Data for Enyne 4: TLC: $R_f$=0.15 (20% EtOAc in hexanes); $^1$H NMR (600 MHz, $CDCl_3$): δ 7.37-7.31 (m, 4H), 7.30-7.27 (m, 1H), 7.20 (t, J=7.8 Hz, 1H), 6.80 (d, J=7.5 Hz, 1H), 6.77-6.73 (m, 2H), 4.87 (s, 1H), 4.83 (s, 1H), 4.50 (s, 2H), 3.83-3.77 (m, 4H), 3.48 (t, J=6.4 Hz, 2H), 2.78 (t, J=7.3 Hz, 2H), 2.47 (t, J=7.4 Hz, 2H), 2.39-2.24 (m, 3H), 2.18-2.09 (m, 3H), 1.95 (d, J=4.0 Hz, 1H), 1.81-1.73 (m, 2H), 1.53 (s, 1H); $^{13}$C NMR (150 MHz, $CDCl_3$): 159.7, 145.8, 142.5, 138.6, 129.5, 128.5, 127.8, 127.7, 120.9, 114.4, 112.6, 111.6, 82.4, 77.1, 73.1, 69.9, 68.0, 55.2, 43.3, 35.5, 32.5, 27.9, 27.3, 20.9; IR (neat, $cm^{-1}$): 3445 (w), 3030 (w), 2934 (s), 2858 (m), 1644 (w), 1602 (m), 1585 (m), 1492 (m), 1454 (m), 1437 (m), 1362 (w), 1261 (s), 1153 (m), 1102 (m), 1052 (s), 896 (w), 778 (w), 738 (m), 697 (s); HRMS (ESI-TOF) (m/z): $[M+H]^+$ calcd for $C_{26}H_{33}O_3$ 393.2430; found, 393.2417;

$$[\alpha]^{22.2}_{589}:$$

−2.392 (c 0.0033, $CHCl_3$).

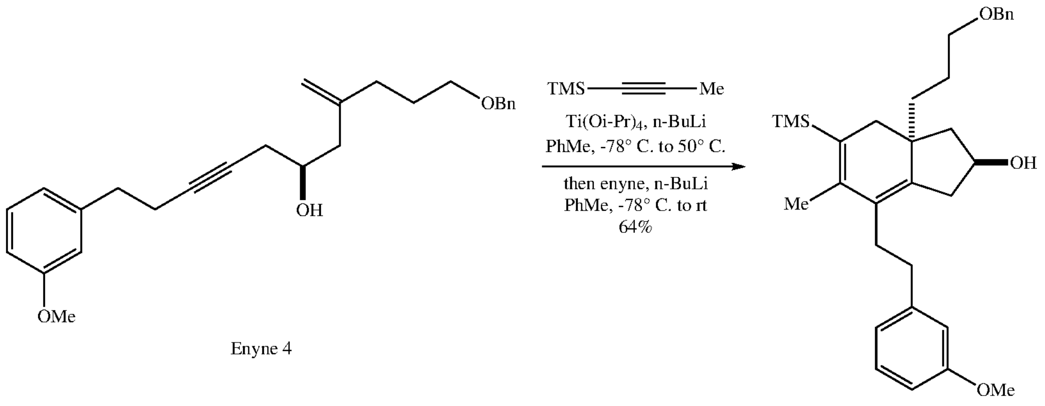

Enyne 4

Hydrindane 4

Synthesis of Hydrindane 4: To a stirred solution of TMS-propyne (707 mg, 6.30 mmol, 3.3 equiv), $Ti(Oi-Pr)_4$ (1.87 mL, 6.30 mmol, 3.3 equiv), and PhMe (42 mL) at −78° C. in a 50 mL round-bottom flask was added n-BuLi (4.89 mL, 12.2 mmol, 6.4 equiv, 2.5 M in hexanes). The solution was allowed to warm to rt, and then heated to 50° C. for 1 h. Following this, the solution was then cooled to rt. At the same time, to Enyne 4 (750 mg, 1.91 mmol, 1.0 equiv) in PhMe (6.4 mL) in a 10 mL round-bottom flask at −78° C. was added n-BuLi (0.764 mL, 1.91 mmol, 1.0 equiv, 2.5 M in hexanes). Following the dropwise addition, the solution was allowed to warm to rt. At rt, the flask containing the enyne was added dropwise to the flask containing the TMS-alkyne. The solution was stirred overnight before the addition of benzaldehyde (0.640 mL, 6.3 mmol, 3.3 equiv), which was stirred for 30 min before the addition of sat. aq. $NaHCO_3$ (10 mL). The biphasic solution was stirred for 30 min before the phases were separated, and the aqueous phase was extracted with EtOAc (3×30 mL). The combined organic phase was dried over $Na_2SO_4$, filtered, and concentrated in vacuo. The resulting crude oil was purified by flash chromatography with a Biotage® Sfär 50 g cartridge and a gradient from 0-35% EtOAc in hexanes to afford Hydrindane 4 (622 mg, 1.23 mmol, 64%) as a pale, yellow oil.

Data for Hydrindane 4: TLC: $R_f$=0.10 (20% EtOAc in hexanes); $^1H$ NMR (600 MHz, $CDCl_3$): δ 7.35-7.29 (m, 5H), 7.18 (t, J=7.8 Hz, 1H), 6.73 (app t, J=6.9 Hz, 2H), 6.67 (s, 1H), 4.46 (s, 2H), 4.32-4.27 (m, 1H), 3.78 (s, 3H), 3.41-3.30 (m, 2H), 2.73-2.60 (m, 1H), 2.60-2.43 (m, 3H), 2.39-2.29 (m, 2H), 2.13 (dd, J=12.8, 5.9 Hz, 1H), 2.07-2.00 (m, 1H), 1.92 (s, 3H), 1.87 (d, J=16.5 Hz, 1H), 1.53 (s, 1H), 1.48-1.38 (m, 2H), 1.38-1.31 (m, 1H), 1.31-1.23 (m, 1H), 1.10-1.01 (m, 2H), 0.15 (s, 9H); $^{13}C$ NMR (150 MHz, $CDCl_3$): 159.6, 144.8, 143.8, 142.1, 138.7, 129.7, 129.3, 128.5, 128.4, 127.7, 127.6, 121.3, 114.8, 111.1, 72.9, 72.3, 71.1, 55.3, 47.6, 42.5, 38.8, 38.3, 35.8, 31.5, 29.2, 25.7, 19.2, 0.3; IR (neat, $cm^{-1}$): 3398 (w), 2947 (s), 1602 (m), 1490 (m), 1454 (s), 1250 (s), 1152 (m), 1052 (m), 839 (s), 753 (m), 698 (s); HRMS (ESI-TOF) (m/z): $[M+H]^+$ calcd for; found;

$$[\alpha]_{589}^{22.3}:$$

−34.693 (c 0.002, $CHCl_3$).

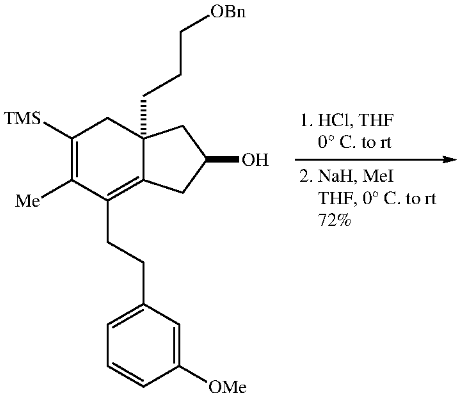

Hydrindane 4

-continued

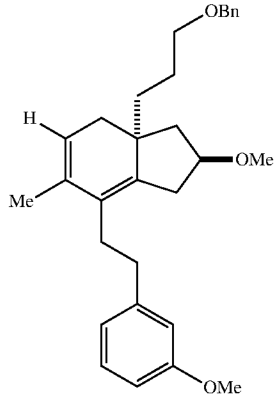

Compound 206

Synthesis of Compound 206: To a stirred solution of Hydrindane 4 (215 mg, 0.426 mmol, 1.0 equiv) at 0° C. in THF (2 mL) was slowly added HCl (2 mL, 2M). The reaction mixture was allowed to slowly warm to rt over 2 h. Following dilution with $H_2O$ (3 mL) and EtOAc (3 mL), the biphasic solution was separated, and the aqueous phase was extracted with EtOAc (3×10 mL). The combined organic phases were dried over $MgSO_4$, filtered, and concentrated in vacuo. The resulting crude oil was purified by flash chromatography with a Biotage® Snap Ultra 25 g cartridge and a gradient from 0-15% EtOAc in hexanes to afford the desilylated hydrindane as a clear oil which was immediately used in the next reaction.

To a stirred solution of desilylated hydrindane in THF (4 mL) at 0° C. was added NaH (51 mg, 1.28 mmol, 3 equiv), and the solution was stirred for 10 min before the addition of MeI (0.159 mL, 2.56 mmol, 6 equiv). The solution was allowed to warm to rt and stirred overnight. Upon completion, the reaction was cooled to 0° C. before being quenched with $H_2O$ (4 mL), the phases were separated, and the aqueous phase was extracted with EtOAc (3×10 mL). The combined organic phase was dried over $Na_2SO_4$, filtered, and concentrated in vacuo. The resulting crude oil was purified by flash chromatography with a Biotage® Sfär 25 g cartridge and a gradient from 0-15% EtOAc in hexanes to afford Compound 206 (137 mg, mmol, 72%) as a pale, yellow oil.

Data for Compound 206: TLC: $R_f$=0.23 (10% EtOAc in hexanes); $^1H$ NMR (600 MHz, $CDCl_3$): δ 7.37-7.31 (m, 4H), 7.30-7.27 (m, 1H), 7.19 (t, J=7.8 Hz, 1H), 6.78 (d, J=7.6 Hz, 1H), 6.75-6.69 (m, 2H), 5.34 (d, J=5.5 Hz, 1H), 4.48 (s, 2H), 3.94 (quint, J=7.1 Hz, 1H), 3.79 (s, 3H), 3.45-3.36 (m, 1H), 3.27 (s, 3H), 2.66-2.52 (m, 3H), 2.40-2.29 (m, 2H), 2.26-2.13 (m, 3H), 2.03-1.97 (m, 1H), 1.80 (s, 3H), 1.55-1.40 (m, 3H), 1.31 (dd, J=12.4, 8.4 Hz, 1H), 1.12-1.05 (m, 1H); $^{13}C$ NMR (150 MHz, $CDCl_3$): 159.6, 143.9, 142.4, 138.7, 133.1, 129.3, 128.4, 128.2, 127.7, 127.6, 121.0, 119.6, 114.6, 111.0, 80.5, 73.0, 71.2, 56.9, 55.2, 44.4, 43.2, 35.7, 34.7, 34.2, 31.8, 29.7, 25.5, 19.4; IR (neat, $cm^{-1}$): 2936 (s), 2859 (m), 1602 (m), 1584 (m), 1490 (m), 1453 (m), 1363 (w), 1261 (m), 1152 (m), 1102 (s), 1054 (m), 779 (w), 737 (m), 697 (m); HRMS (ESI-TOF) (m/z): $[M+H]^+$ calcd for; found;

$$[\alpha]_{589}^{22.4}:$$

−133.840 (c 0.00014, $CHCl_3$).

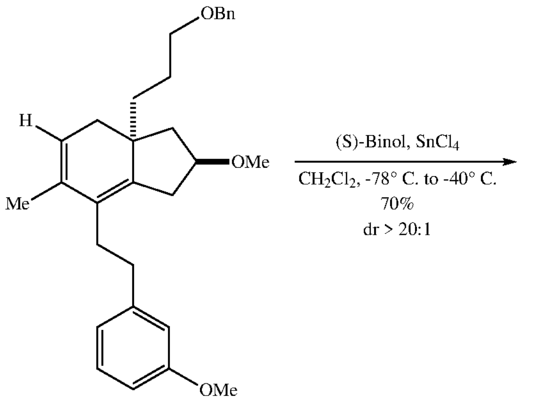

Compound 206

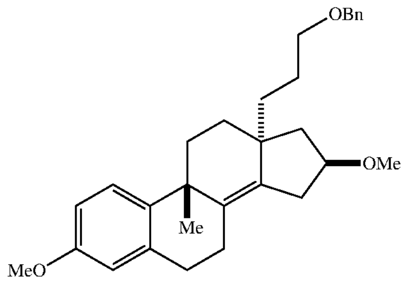

Compound 306

Synthesis of Compound 306: To a stirred solution of (S)-BINOL (36 mg, 0.104 mmol, 1.2 equiv) in $CH_2Cl_2$ (1.1 mL) at −78° C. was added $SnCl_4$ (0.104 mL, 0.104 mmol, 1.0 equiv, 1.0 M in $CH_2Cl_2$) which was stirred for 30 min at that temperature before the addition of Compound 206 (46.6 mg, 0.104 mmol, 1.0 equiv) in $CH_2Cl_2$ (1.0 mL), and the solution was kept at that temperature for 15 min before being transferred to a −40° C. bath. After 1 h, the reaction mixture was quenched with sat. aq. $NH_4Cl$ (2 mL) and allowed to warm to rt. The biphasic solution was stirred for 1 h before being transferred to a separatory funnel where the phases were separated, and the aqueous phase was extracted with $CH_2Cl_2$ (3×10 mL). The combined organic phase was washed with 5 mol % NaOH (1 mL), was dried over $MgSO_4$, filtered, and concentrated in vacuo. The resulting crude product was purified by flash chromatography with a Biotage® Snap Ultra 25 g column and a gradient from 0-5% EtOAc in hexanes additive to afford Compound 306 (32.5 mg, 0.0728 mmol, 70%) as a clear oil.

Data for Compound 306: TLC: $R_f$=0.20 (10% EtOAc in hexanes); $^1$H NMR (600 MHz, $CDCl_3$): δ 7.37-7.25 (m, 5H), 7.21 (d, J=8.6 Hz, 1H), 6.77 (d, J=8.5 Hz, 1H), 6.60 (s, 1H), 4.47 (s, 2H), 4.06 (quint, J=6.8 Hz, 1H), 3.79 (s, 3H), 3.24-3.35 (m, 2H), 3.33 (s, 3H), 2.90 (dd, J=15.8, 2.9 Hz, 1H), 2.81-2.69 (m, 2H), 2.48-2.42 (m, 1H), 2.41-2.30 (m, 3H), 2.04 (d, J=13.2 Hz, 1H), 1.92 (d, J=13.3 Hz, 1H), 1.80 (t, J=13.6 Hz, 1H), 1.59-1.50 (m, 3H), 1.33 (s, 3H), 1.32-1.24 (m, 1H), 1.21-1.13 (m, 2H); $^{13}$C NMR (150 MHz, $CDCl_3$): 157.1, 140.2, 138.6, 137.3, 136.7, 131.9, 128.4, 127.6, 127.2, 113.0, 112.5, 80.1, 73.0, 71.0, 56.9, 55.2, 44.1, 44.0, 38.0, 34.4, 34.0, 32.3, 31.8, 31.5, 29.0, 25.0, 25.0; IR (neat, $cm^{-1}$): 2932 (s), 2859, 1608 (w), 1498 1608 (m), 1454 (m), 1365 (w), 1273 (m), 1247 (m), 1231 (m), 1100 (s), 1038 (w), 736 (w), 698 (w); HRMS (ESI-TOF) (m/z): $[M+H]^+$ calcd for $C_{30}H_{39}O_3$ 447.2899; found, 447.2892;

$$[\alpha]_{589}^{22.6}:$$

−97.146 (c 0.0019, $CHCl_3$).

5C. Compound 307—(9R,13S,16R)-3,16-dimethoxy-9,13-dimethyl-7,9,11,12,13,15,16,17-octahydro-6H-cyclopenta[α]phenanthrene

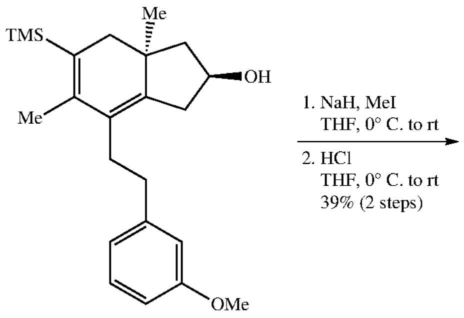

Hydrindane 5

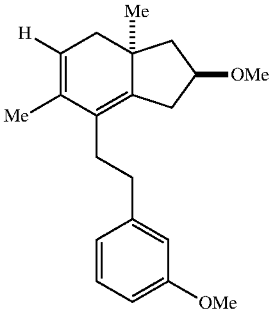

Compound 207

Synthesis of Compound 207: To a stirred solution of hydrindane (500 mg, 1.35 mmol, 1.0 equiv) at 0° C. in THF (5 mL) was slowly added HCl (5 mL, 2M). The reaction mixture was allowed to slowly warm to rt over 2 h. Following dilution with sat. aq. $NaHCO_3$ (10 mL) and EtOAc (10 mL), the biphasic solution was separated, and the aqueous phase was extracted with EtOAc (3×20 mL). The combined organic phases were dried over $MgSO_4$, filtered, and concentrated in vacuo. The resulting crude oil was purified by flash chromatography with a Biotage® Snap Ultra 25 g cartridge and a gradient from 0-35% EtOAc in hexanes to afford the desilylated hydrindane as a clear oil which was immediately used in the next reaction.

To a stirred solution of desilylated hydrindane in THF (27 mL) at 0° C. was added NaH (270 mg, 6.75 mmol, 5 equiv), and the solution was stirred for 10 min before the addition of MeI (1.00 mL, 16.2 mmol, 12 equiv). The solution was allowed to warm to rt and stirred overnight. Upon completion, the reaction was cooled to 0° C. before being quenched with $H_2O$ (10 mL), the phases were separated, and the aqueous phase was extracted with EtOAc (3×20 mL). The combined organic phase was dried over $Na_2SO_4$, filtered, and concentrated in vacuo. The resulting crude oil was purified by flash chromatography with a Biotage® Sfär 25 g cartridge and a gradient from 0-15% EtOAc in hexanes to afford Compound 207 (163 mg, 0.522 mmol, 39%) as a pale, yellow oil.

Data for Compound 207: TLC: $R_f$=0.29 (5% EtOAc in hexanes); $^1$H NMR (600 MHz, $CDCl_3$): δ 7.19 (t, J=7.8 Hz, 1H), 6.78 (d, J=7.7 Hz, 1H), 6.75-6.69 (m, 2H), 5.39 (d, J=6.1 Hz, 1H), 3.98 (quint, J=7.4 Hz, 1H), 3.79 (s, 3H), 3.30 (s, 3H), 2.66 (dd, J=17.3, 7.9 Hz, 1H), 2.62-2.53 (m, 2H), 2.39-2.28 (m, 2H), 2.15-2.01 (m, 4H), 1.82 (s, 3H), 1.41 (t, J=10.3 Hz, 1H), 0.88 (s, 3H); $^{13}C$ NMR (150 MHz, $CDCl_3$): 159.7, 144.0, 142.4, 132.7, 129.3, 127.7, 121.1, 119.8, 114.6, 111.1, 80.4, 57.0, 55.3, 47.8, 40.0, 37.7, 35.6, 34.6, 31.8, 22.3, 19.4; IR (neat, $cm^{-1}$): 3376 (m, br), 2935 (s), 2834 (w), 1734 (m), 1602 (m), 1585 (m), 1489 (m), 1455 (m), 1437 (m), 1374 (m), 1315 (w), 1260 (s), 1191 (w), 1153 (m), 1094 (m), 1047 (m), 756 (m), 698 (m); HRMS (ESI-TOF) (m/z): $[M+H]^+$ calcd for $C_{21}H_{29}O_2$ 313.2168; found, 313.2154;

$$[\alpha]^{22.5}_{589}:$$

−3.768(c 0.00135, $CHCl_3$).

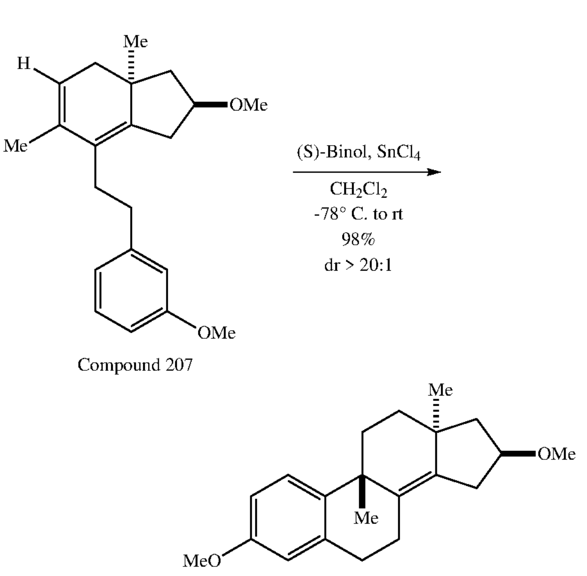

Compound 207

Compound 307

Synthesis of Compound 307: To a stirred solution of (S)-BINOL (28.3 mg, 0.0.0987 mmol, 1.2 equiv) in $CH_2Cl_2$ (1.0 mL) at −78° C. was added $SnCl_4$ (0.82 mL, 0.0823 mmol, 1.0 equiv, 1.0 M in $CH_2Cl_2$) which was stirred for 30 min at that temperature before the addition of Compound 207 (25.7 mg, 0.0823 mmol, 1.0 equiv) in $CH_2Cl_2$ (0.5 mL), and the solution was kept at that temperature for 1 h before being allowed to warm to rt. After 1 h, the reaction mixture was quenched with sat. aq. $NH_4Cl$ (2 mL). The biphasic solution was stirred for 1 h before being transferred to a separatory funnel where the phases were separated, and the aqueous phase was extracted with $CH_2Cl_2$ (3×10 mL). The combined organic phase was washed with 5 mol % NaOH (1 mL), was dried over $MgSO_4$, filtered, and concentrated in vacuo. The resulting crude product was filtered through silica to afford Compound 307 (25.3 mg, 0.0810 mmol, 98%) as a clear oil.

Data for Compound 307: TLC: $R_f$=0.30 (10% EtOAc in hexanes); $^1H$ NMR (600 MHz, $CDCl_3$): δ 7.22 (d, J=8.7 Hz, 1H), 6.76 (dd, J=8.4, 2.6 Hz, 1H), 6.59 (d, J=2.3 Hz, 1H), 4.16-4.10 (m, 1H) 3.78 (s, 3H), 3.34 (s, 3H), 2.91-2.85 (m, 1H), 2.81-2.68 (m, 2H), 2.46-2.41 (m, 1H), 2.39-2.30 (m, 2H), 2.16 (dd, J=11.7, 6.7 Hz, 1H), 2.09 (dt, J=13.2, 3.2 Hz, 1H), 1.88-1.81 (m, 1H), 1.74-1.69 (m, 2H), 1.14-1.13 (m, 4H), 0.90 (s, 3H); $^{13}C$ NMR (150 MHz, $CDCl_3$): 157.1, 140.2, 137.3, 136.1, 131.7, 127.2, 113.1, 112.5, 80.3, 56.9, 55.3, 48.7, 41.2, 38.1, 34.4, 33.3, 32.3, 31.3, 29.8, 25.8, 25.0; IR (neat, $cm^{-1}$): 2931 (s), 1608 (m), 1498 (s), 1455 (m), 1372 (w), 1273 (m), 1232 (m), 1101 (m), 1038 (m); HRMS (ESI-TOF) (m/z): $[[M+H]^+$ calcd for $C_{21}H_{29}O_2$ 313.2168; found, 313.2159;

$$[\alpha]^{22.6}_{589}:$$

−154.092 (c 0.00007, $CHCl_3$).

Example 6. General Materials and Methods

Stereochemical Relationships. All stereochemical relationships are the result of characterization studies from both 1D and 2D NMR studies. The relative stereochemistry between the C9 and 13 substituents was established via 1D nOe experiments, unless otherwise indicated.

Experimental Setups. All reactions were conducted in flame-dried glassware under an atmosphere of nitrogen and in anhydrous solvents unless otherwise indicated. Later examples utilized silylated glassware, azeotropically dried starting materials, and vacuum-dried BINOL-reagents. All reagents and starting materials were purchased from commercial sources and used as received, unless otherwise indicated. Anhydrous dichloromethane ($CH_2Cl_2$), diethyl ether ($Et_2O$), tetrahydrofuran (THF), and toluene (PhMe) were obtained by passing commercially available HPLC grade solvents through a column of activated alumina using a Glass Contour Solvent Purification System by Pure Process Technology LLC. Titanium isopropoxide ($Ti(Oi\text{-}Pr)_4$) was distilled prior to use and stored in a foil-wrapped round bottom flask under an atmosphere of nitrogen. Said flask was stored in a desiccator when not in use. n-BuLi was purchased from Sigma-Aldrich as a 2.5 M solution in hexanes, and was titrated against N-benzylbenzamide according to a literature procedure (Burchat, A. F.; Chong, J. M. Titration of Alkyllithiums with a Simple Reagent to a Blue Endpoint. *J. Organomet. Chem.* 1997, 542, 281-283) to accurately determine the titer before use. Percent yields correspond to chromatographically and spectroscopically ($^1H$ NMR) homogeneous materials, unless otherwise stated. Flash chromatography was performed on a Biotage® Automated Liquid Chromatography System Isolera One® using Biotage® SNAP KP-Sil 10-25 g or Biotage® SNAP Ultra 25 μm HP-Sphere 10-50 g silica gel cartridges or performed using a forced flow of the indicated solvent system on Sorbent Technologies™ silica gel 60 Å (40-63 μm particle size). Thin phase chromatography (TLC) analyses were performed on EMD TLC silica gel 60 $F_{234}$ glass plates and the compounds were visualized by exposure to UV light (254 nm) followed by staining with p-anisaldehyde, cerium ammonium molybdate, or $KMnO_4$.

Spectral Analysis Information. $^1H$ NMR spectra were recorded on a Bruker Avance III 500 MHz (TBI probe) or a 600 MHz (BBFO probe) spectrometer in chloroform-d ($CDCl_3$). All signals are reported in parts per million (ppm) and calibrated to the residual protium signal of chloroform ($CHCl_3$, 7.26 ppm). Signals are reported as δ chemical shifts in ppm (multiplicity, coupling constants in Hz, integration). $^{13}C$ NMR spectra were recorded on a Bruker Avance III 600 MHz (BBFO probe) spectrometer measured at 150 MHz or a Bruker Avance III 500 MHz (TBI probe) spectrometer measured at 125 MHz. All signals are reported in ppm and are calibrated to the central line of the residual solvent signal of $CHCl_3$ (77.16 ppm). Signals are reported as δ chemical shift(s) in ppm. Two-dimensional NMR spectra, including COSY, HSQC, HMBC, and NOESY were recorded on a Bruker Avance III 600 MHz spectrometer (BBFO probe), or a Bruker Avance III 500 MHz spectrometer (TBI probe). Infrared spectra were recorded on a JASCO FT/IR-4100 Fourier Transform Infrared Spectrometer. IR absorption is reported as strong (s), medium (m), weak (w), or broad (br). ESI-TOF high-resolution mass spectroscopy (HRMS) analyses were performed at the mass spectrometry laboratory of the University of Illinois at Urbana-Champaign. Optical rotations ([α]) were obtained on a JASCO P-2000 polarimeter equipped with tungsten-halogen lamp (WI) and interface filter set to 589 nm, using a sample cell with a pathlength of 100 mm. Specific rotations are reported as:

$$[\alpha]_{589}^{T(^{\circ}C)}$$

(c, solvent) and are based on the equation $$[[\alpha]_{589}^{T(^{\circ}C))} =$$

(100·[α])/(I·c), where the concentration (c) is reported as g/2 mL and the pathlength (I) is in decimeters.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A compound or pharmaceutically acceptable salt thereof, wherein the compound has a structure corresponding to Formula (IV-A1):

(IV-A1)

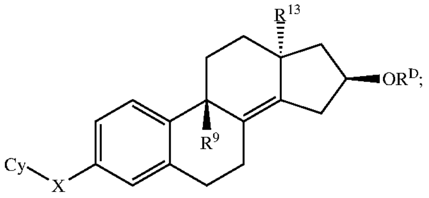

wherein Cy is an optionally substituted mono- or polycyclic moiety selected from the group consisting of $C_{6-15}$-aryl, 5-to 15-membered heteroaryl, $C_{3-15}$-cycloalkyl, $C_{3-15}$-cycloalkenyl, 3-to 15-membered heterocycloalkyl, and 3- to 15-membered heterocycloalkenyl;

X is absent or selected from the group consisting of —$NR^Z$—, —$C(R^Z)_2$—, —O—, —C(O)—, and —$S(O)_y$—, wherein each $R^Z$ is independently hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, or $C_{3-8}$-cycloalkyl, and y is 0, 1, or 2;

$R^9$ is $C_{1-10}$-alkyl or $C_{1-10}$-haloalkyl, each of which is optionally interrupted by one or more of —O—, —$NR^Z$—, —C(O)—, —C(O)O—, —OC(O)—, —$C(O)NR^Z$—, and —$NR^ZC(O)$—; or $R^9$ is

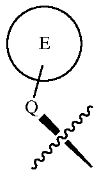

wherein Q is absent or selected from the group consisting of $C_1$-$C_{10}$-alkylene, $C_1$-$C_{10}$-haloalkylene, $C_2$-$C_{10}$-alkenylene, $C_2$-$C_{10}$-haloalkenylene, $C_2$-$C_{10}$-alkynylene, $C_2$-$C_{10}$-haloalkynylene, each of which is optionally interrupted by one or more of —O—, —$NR^Z$—, —C(O)—, —C(O)O—, —OC(O)—, —$C(O)NR^Z$—, —$NR^ZC(O)$—, —$S(O)_y$—, —$S(O)_yNR^Z$—, —$NR^ZS(O)_y$—, —$C(S)NR^Z$—, —$NR^ZC(S)$—; and E is selected from the group consisting of $C_{6-10}$-aryl, 5- to 10-membered heteroaryl, $C_{3-8}$-cycloalkyl, or 3- to 8-heterocycloalkyl;

$R^{13}$ is selected from the group consisting of $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, each of which is optionally interrupted by one or more of —O—, —$NR^Z$—, —C(O)—, —C(O)O—, —OC(O)—, —$C(O)NR^Z$—, —$NR^ZC(O)$—, —$S(O)_y$—, —$S(O)_yNR^Z$—, —$NR^ZS(O)_y$, —$C(S)NR^Z$—, and —$NR^ZC(S)$—;

$R^D$ is selected from the group consisting of hydrogen $C_{1-10}$-alkyl, $C_{1-10}$-haloalkyl, $C_{2-10}$-alkenyl, $C_{2-10}$-haloalkenyl, $C_{2-10}$-alkynl, $C_{2-10}$-haloalkynyl, —$(CH_2)_m$-$C_{6-10}$-aryl, —$(CH_2)_m$-5- to 10-membered heteroaryl;

m is an integer selected from the group consisting of 0, 1, 2, and 3;

wherein any $C_{6-10}$-aryl, 5- to 10-membered heteroaryl, $C_{3-8}$-cycloalkyl, or 3- to 8-heterocycloalkyl is optionally substituted with one or more halogen, hydroxy, $C_{1-6}$-alkyl, $C_{1-6}$-haloalkyl, or $C_{1-6}$-alkoxy.

2. The compound or pharmaceutically acceptable salt of claim 1, wherein

Cy is an optionally substituted monocyclic 5- or 6-membered heteroaryl;

X is absent or —$NR^Z$—;

$R^9$ is

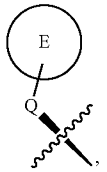

wherein Q is absent, $C_1$-$C_3$-alkylene, or $C_1$-$C_3$-haloalkylene and E is an optionally substituted $C_{6-10}$-aryl;
$R^{13}$ is $C_1$-$C_3$-alkyl or $C_1$-$C_3$-haloalkyl; and
$R^D$ is hydrogen, $C_{1-3}$-alkyl, or $C_{1-3}$-haloalkyl.

3. The compound or pharmaceutically acceptable salt of claim 1, wherein
Cy is an optionally substituted monocyclic 5- or 6-membered heteroaryl;
X is absent or —$NR^Z$—;
$R^9$ is

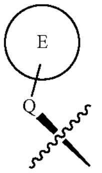

wherein Q is absent, $C_1$-$C_{10}$-alkylene, or $C_1$-$C_{10}$-haloalkylene, each of which is optionally interrupted by one or more of —O—, —$NR^Z$—, —C(O)—, —C(O)O—, —OC(O)—, —C(O)$NR^Z$—, and —$NR^Z$C(O)—; and E is an optionally substituted $C_{6-10}$-aryl.

4. The compound or pharmaceutically acceptable salt of claim 1, wherein $R^D$ is hydrogen, $C_{1-10}$-alkyl, or $C_{1-10}$-haloalkyl.

5. The compound or pharmaceutically acceptable salt of claim 1, wherein $R^{13}$ is $C_1$-$C_{10}$-alkyl or $C_1$-$C_{10}$-haloalkyl, each of which is optionally interrupted by one or more of —O—, —$NR^Z$—, —C(O)—, —C(O)O—, —OC(O)—, —C(O)$NR^Z$—, and —$NR^Z$C(O)—.

6. The compound or pharmaceutically acceptable salt of claim 1, wherein the compound has a structure corresponding to:

101

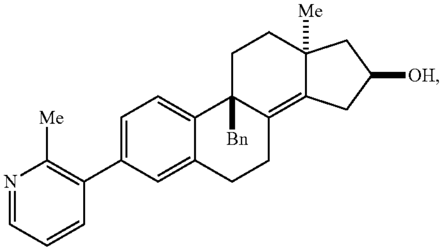

102

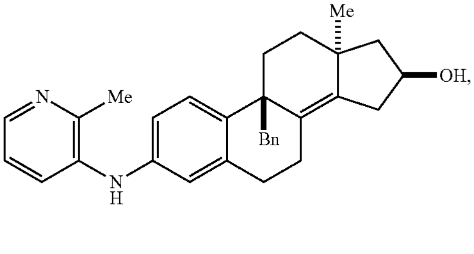

-continued

103

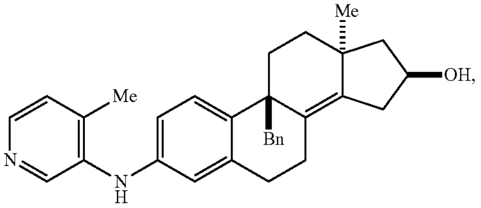

104

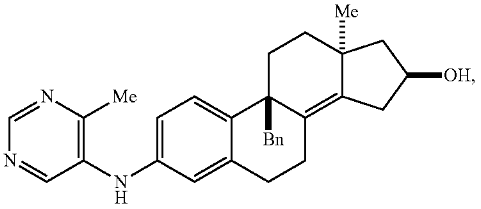

105

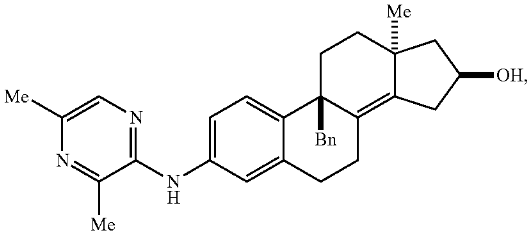

or

106

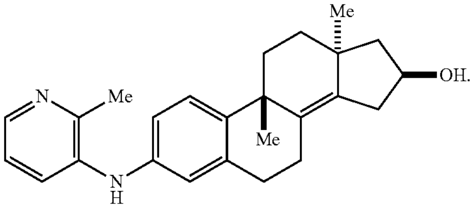

7. A pharmaceutical composition comprising (i) a compound of claim 1, or pharmaceutically acceptable salt or prodrug thereof and (ii) a pharmaceutically acceptable excipient.

8. The compound or pharmaceutically acceptable salt of claim 1, wherein
Cy is selected from the group consisting of pyridinyl, pyridazinyl, pyrimidinyl, and
pyrazinyl and Cy is optionally substituted with one or more $C_{1-6}$-alkyl;
X is absent or —$NR^Z$—;
$R^9$ is

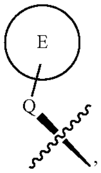

wherein Q is absent, $C_1$-$C_3$-alkylene, or $C_1$-$C_3$-haloalkylene and E is an optionally substituted $C_{6-10}$-aryl;
$R^{13}$ is $C_1$-$C_3$-alkyl or $C_1$-$C_3$-haloalkyl; and
$R^D$ is hydrogen, $C_{1-3}$-alkyl, or $C_{1-3}$-haloalkyl.

9. The compound or pharmaceutically acceptable salt of claim 1, wherein

Cy is selected from the group consisting of pyridinyl, pyridazinyl, pyrimidinyl, and pyrazinyl and Cy is optionally substituted with one or more $C_{1-6}$-alkyl;

X is —$NR^Z$—;

$R^9$ is

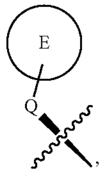

wherein Q is absent, $C_1$-$C_3$-alkylene, or $C_1$-$C_2$-haloalkylene and E is an optionally substituted $C_{6-10}$-aryl;

$R^{13}$ is $C_1$-$C_3$-alkyl or $C_1$-$C_3$-haloalkyl; and $R^D$ is hydrogen, $C_{1-3}$-alkyl, or $C_{1-3}$-haloalkyl.

10. The compound or pharmaceutically acceptable salt of claim 1, wherein Cy is selected from the group consisting of pyridinyl, pyridazinyl, pyrimidinyl, and pyrazinyl and Cy is optionally substituted with one or more $C_{1-6}$-alkyl;

X is —$NR^Z$—;

$R^9$ is

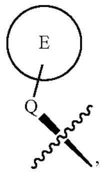

wherein Q is $C_1$-$C_3$-alkylene, or $C_1$-$C_3$-haloalkylene and E is an optionally substituted $C_{6-10}$-aryl;

$R^{13}$ is $C_1$-$C_3$-alkyl or $C_1$-$C_3$-haloalkyl; and $R^D$ is hydrogen, $C_{1-3}$-alkyl, or $C_{1-3}$-haloalkyl.

11. The compound or pharmaceutically acceptable salt of claim 1, wherein Cy is selected from the group consisting of pyridinyl, pyrimidinyl, and pyrazinyl and Cy is optionally substituted with one or more $C_{1-6}$-alkyl;

X is —$NR^Z$—;

$R^9$ is

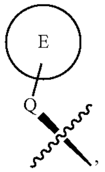

wherein Q is $C_1$-$C_3$-alkylene, or $C_1$-$C_3$-haloalkylene and E is an unsubstituted $C_{6-10}$-aryl;

$R^{13}$ is $C_1$-$C_3$-alkyl or $C_1$-$C_3$-haloalkyl; and $R^D$ is hydrogen, $C_{1-3}$-alkyl, or $C_{1-3}$-haloalkyl.

12. The compound or pharmaceutically acceptable salt of claim 1, wherein Cy is pyridinyl and Cy is optionally substituted with one or more $C_{1-6}$-alkyl;

X is —$NR^Z$—;

$R^9$ is

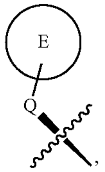

wherein Q is $C_1$-$C_3$-alkylene, or $C_1$-$C_3$-haloalkylene and E is phenyl;

$R^{13}$ is $C_1$-$C_3$-alkyl or $C_1$-$C_3$-haloalkyl; and $R^D$ is hydrogen.

13. A pharmaceutical composition comprising (i) a compound of claim 12, or pharmaceutically acceptable salt thereof and (il) a pharmaceutically acceptable excipient.

* * * * *